(12) United States Patent
An et al.

(10) Patent No.: US 11,839,216 B1
(45) Date of Patent: Dec. 12, 2023

(54) QUINOLINE-2,3-FUSED NINE-MEMBERED RING SCAFFOLD COMPOUND, AND PREPARATION METHOD AND APPLICATION THEREOF AS EFFECTIVE COMPONENT IN PLANT FUNGICIDE

(71) Applicant: QINGDAO AGRICULTURAL UNIVERSITY, Qingdao (CN)

(72) Inventors: Xiao-De An, Qingdao (CN); Jian Xiao, Qingdao (CN); Daying Shao, Qingdao (CN); Bin Qiu, Qingdao (CN)

(73) Assignee: QINGDAO AGRICULTURAL UNIVERSITY, Shandong (CN)

( * ) Notice: Subject to any disclaimer, the term of this patent is extended or adjusted under 35 U.S.C. 154(b) by 0 days.

(21) Appl. No.: 18/166,346

(22) Filed: Feb. 8, 2023

Related U.S. Application Data

(63) Continuation of application No. PCT/CN2022/018299, filed on Sep. 13, 2022.

(30) Foreign Application Priority Data

Aug. 23, 2022 (CN) .......................... 202211014099.1
Aug. 23, 2022 (CN) .......................... 202211017425.4

(51) Int. Cl.
*C07D 471/14* (2006.01)
*A01N 43/90* (2006.01)
*A01P 3/00* (2006.01)

(52) U.S. Cl.
CPC ............... *A01N 43/90* (2013.01); *A01P 3/00* (2021.08); *C07D 471/14* (2013.01)

(58) Field of Classification Search
CPC .............................. C07D 471/14; A01N 43/90

USPC .................................. 540/460, 461; 504/101
See application file for complete search history.

(56) References Cited

FOREIGN PATENT DOCUMENTS

| CN | 1228084 A | 9/1999 |
|----|-----------|--------|
| CN | 112209948 A | 1/2021 |

OTHER PUBLICATIONS

An, X-D et al.: Hydride transfer-initiated cross-dehydrogenative coupling reaction to access nine-membered rings. Organic Letters, vol. 25, pp. 2432-2437, 2023.*

* cited by examiner

*Primary Examiner* — Charanjit Aulakh
(74) *Attorney, Agent, or Firm* — SZDC LAW P.C.

(57) ABSTRACT

The present disclosure discloses a quinoline-2,3-fused nine-membered ring scaffold compound, and a preparation method and application thereof as an effective component in a plant fungicide. The quinoline-2,3-fused nine-membered ring scaffold compound stated in the present disclosure is prepared by the following method including steps: mixing a quinoline-derived aniline compound and a formaldehyde compound, adding a solvent and a catalyst, controlling a system temperature, and reacting with stirring to obtain a quinoline-2,3-fused nine-membered ring compound. According to the present disclosure, a 1,6-hydride transfer/cyclization strategy is triggered by aldimine condensation, the quinoline-derived aniline compound and the formaldehyde compound are prepared into the quinoline-2,3-fused nine-membered ring compound with a wide substrate scope and a potential biological activity by a "one-pot synthesis method" quickly. The quinoline-2,3-fused nine-membered ring compound shows an excellent inhibitory activity against *G. graminis, C. gloeosporioides, B. cinerea, V. mali, F. oxysporum* and other plant disease-related fungi.

15 Claims, 1 Drawing Sheet

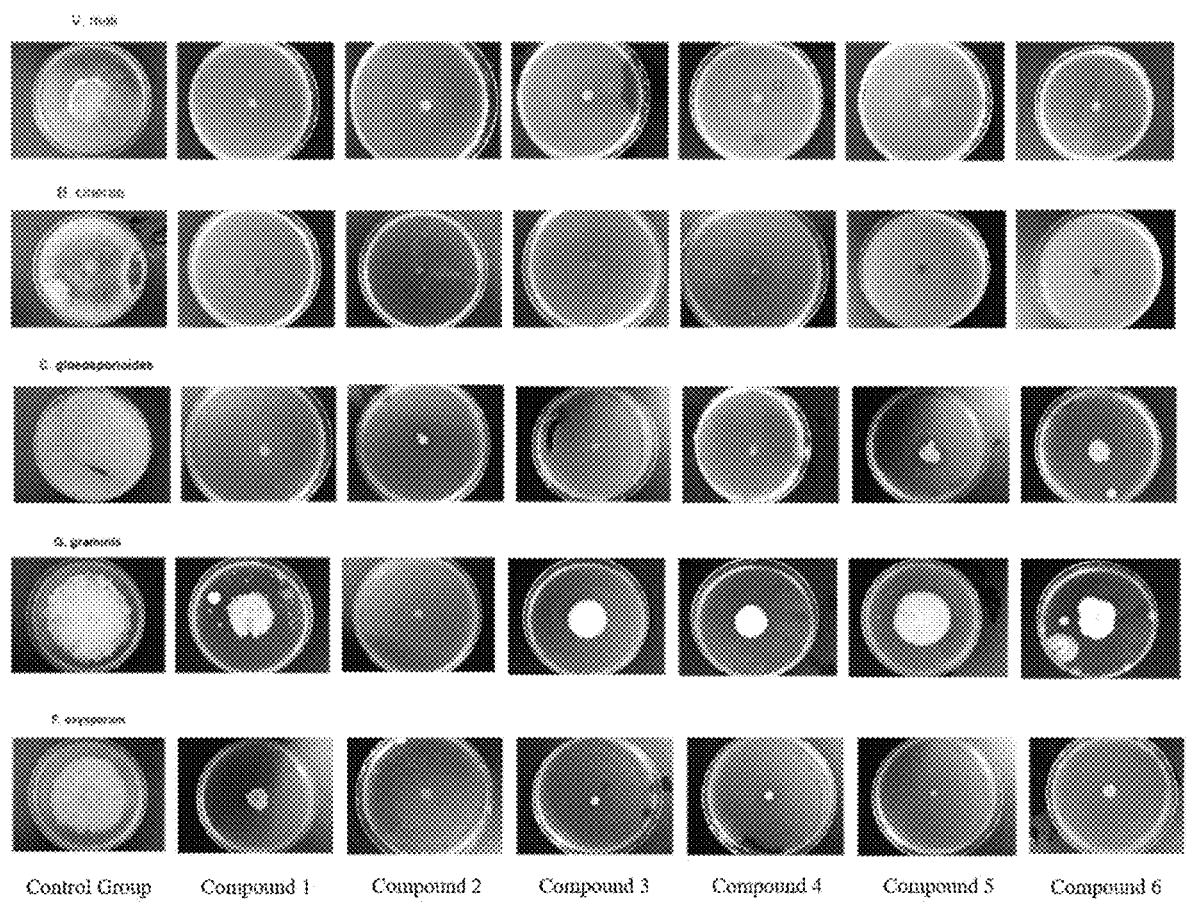

QUINOLINE-2,3-FUSED NINE-MEMBERED RING SCAFFOLD COMPOUND, AND PREPARATION METHOD AND APPLICATION THEREOF AS EFFECTIVE COMPONENT IN PLANT FUNGICIDE

This application is a Continuation Application of PCT/CN2022/118299, filed on Sep. 13, 2022, which claims priority to Chinese Patent Application Nos. CN 202211014099.1, filed on Aug. 23, 2022, and CN 202211017425.4, filed on Aug. 23, 2022, all of which are incorporated by reference for all purposes as if fully set forth herein.

TECHNICAL FIELD

The present disclosure belongs to the technical field of organic synthesis, and particularly relates to a quinoline-2,3-fused nine-membered ring scaffold compound, and a preparation method and application thereof.

BACKGROUND

Quinoline scaffolds are abundant in natural products and alkaloids. Among various quinoline derivatives, 2,3-quino-aza scaffolds are more common and important core scaffolds. Nine-membered medium-ring aza scaffolds also have many active molecules in the natural products. The two scaffolds are widely applied in the field of medicinal chemistry; for example, Taberbovines A shows a good inhibitory activity in RAW264.7 macrophages induced by LPS (Org. Lett. 2019, 21, 4554). In addition, Camptothecin (CPT) alkaloid is a DNA topoisomerase I (Topo I) inhibitor, with an $IC_{50}$ value of 679 nM. The CPT has anti-tumor activities against colorectal cancer, breast cancer, lung cancer and ovarian cancer, and is capable of adjusting a hypoxia-inducible factor-1α (HIF-1α) activity through change of an expression pattern of miRNA in human cancer cells (J. Med. Chem., 1995, 38, 395; Mol. Cancer Ther., 2014, 13, 239; J. Natl. Cancer Inst., 2008, 100, 862). Melohenine B has good anti-tumor, antimitotic and antibacterial activities (Org. Lett., 2009, 11, 4834). Palhinine A is a natural product separated from a plant (Genus *Lycopodium*), and the related activity is still under further investigation. However, the alkaloids with the same type of distinctive polyfused bridging scaffolds have impressive biological activities, including an antimicrobial activity, an anti-HIV-1 activity, enhanced mRNA expression of nerve growth factors and inhibitory activity of acetylcholinesterase (Molecules 2020, 25, 4211).

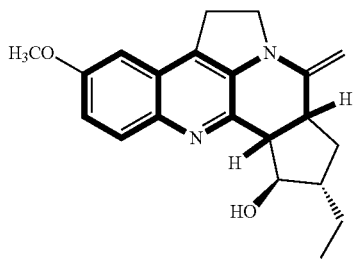

Taberbovines A
Inhibits cellular NO formation

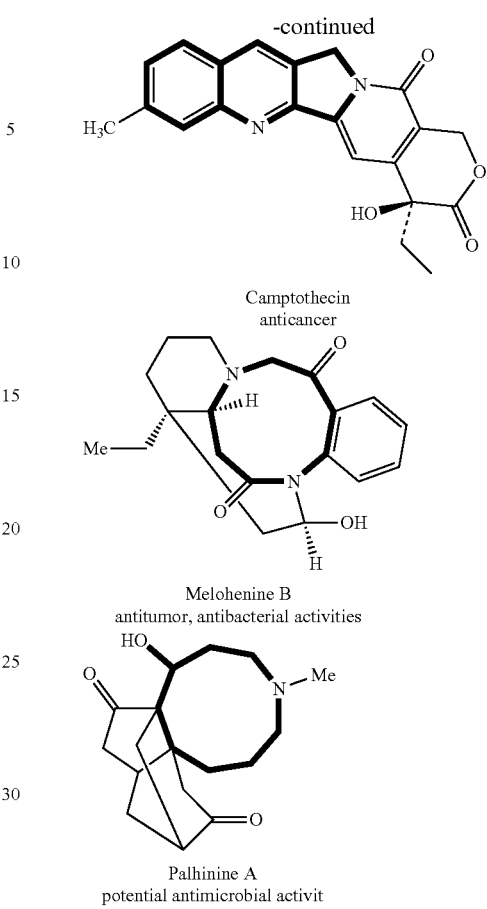

Camptothecin
anticancer

Melohenine B
antitumor, antibacterial activities

Palhinine A
potential antimicrobial activit

It can be known from the above content that both the quinoline scaffold and the nine-membered medium-ring aza scaffold have a great development potential in terms of biological activities. Therefore, it is very important to design and synthesize quino-nine-membered ring scaffold compounds and construct synthesis methods thereof based on the two scaffold constructions for promoting research and development of new drugs, while newly synthesized scaffold molecules also provide much selectable space for screening of drug activities.

In recent years, many efficient strategies for quickly constructing a quinoline polycyclic system were also reported.

In 2020, Ji Shunjun, et al. achieved a unique cascade rearrangement reaction leveraged by methanol. Under catalyst-free and mild reaction conditions, 3-(2-isocyanoethyl)indole and azomethine ylide reacted in the methanol to obtain polycyclic pyrrole[2,3-c]quinoline compounds at a medium-to-high yield (Angew. Chem. Int. Ed. 2020, 59, 21425).

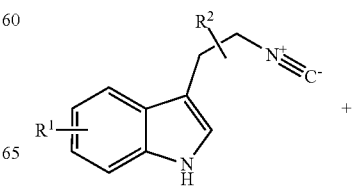

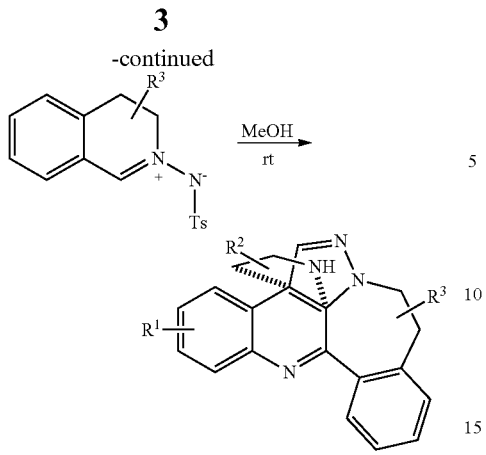

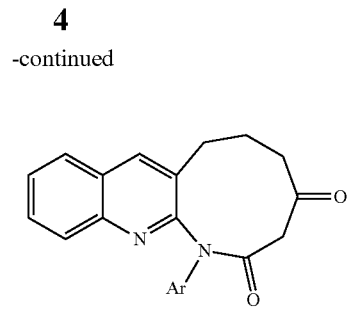

In 2019, Saeed Balalaie, et al. prepared quino-eight-membered rings from 2-alkynylquinoline-3-formaldehyde through a two-step reaction. Firstly, Ugi-4CR was conducted in the methanol by using the 2-alkynylquinoline-3-formaldehyde, 2-iodobenzoic acid, benzylamine and t-butylisonitrile. Then, precipitated adduct 2-alkynylquinoline derivatives were separated therefrom, and directly subjected to reductive cyclization under catalysis of palladium. The cyclization was achieved in DMF/water mixtures by using sodium formate in the presence of Pd(PPh3)4 as a catalyst (J. Org. Chem., 2019, 84, 1074).

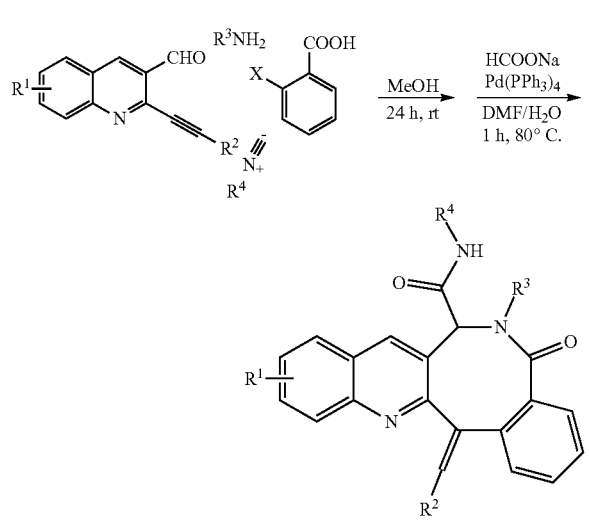

In 2018, Liu Xinyuan, et al. directly synthesized various synthetically challenging heteroaryl fused lactams from existing quinoline nine-membered ring ketone through rare long-distance radical heteroaryl shift in combination with a potocatalytic ring expansion strategy based on substrate design (Angew. Chem. Int. Ed. 2018, 57, 14225).

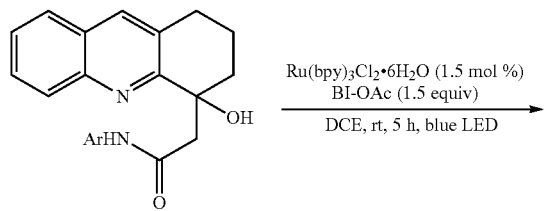

After long-time investigation and exploration by many chemists mentioned above, a great progress has been made in the fusion of the quino-aza medium-ring compound. The quino-aza medium-ring scaffold is the core design of the alkaloids. However, due to an increase in a ring strain and an entropy, the synthesis methodology is challenging. From the above examples, it is not difficult to find that most methods were conducted under metal catalysis. Due to adverse entropy effects and transannular strain effect, there are fewer reports on synthesis research of 2,3-quino-nine-membered rings. Recently, the hydride transfer (HT) reaction has proven to be an efficient strategy to construct a complex polycyclic system. Therefore, a hydride transfer reaction was developed for constructing the quinoline-2,3-fused nine-membered ring scaffold, which is unprecedented in organic synthetic chemistry, and has a potential application value.

Plant fungal diseases imply that invasion of fungi causes damage to normal physiological functions of the plants, even death of the plants in the growth and development process of the plants. Common plant disease-related fungi include C. gloeosporioides, V. mali, F. oxysporum, B. cinerea, G. graminis and the like. The crop loss caused by the plant fungus diseases every year accounts for 10% to 15% of total agricultural yield. Therefore, economic losses may be effectively reduced by timely control over plant fungus diseases. Chemical fungicides are the most cost-effective method for prevention and control of plant diseases due to the characteristics of high efficiency, speed, operability and the like.

SUMMARY OF THE DISCLOSURE

The present disclosure constructs a quinoline-2,3-fused nine-membered ring scaffold, a synthetic method thereof is simple, practical and efficient, and the reaction has the advantages of excellent atom economy, environmental friendliness and the like. Moreover, in synthesis research of the quinoline-2,3-fused nine-membered ring compound, it is found that the quinoline-2,3-fused nine-membered ring compound has higher bactericidal activity, and especially shows an excellent inhibitory activity against C. gloeosporioides, V. mali, F. oxysporum, B. cinerea, G. graminis and other plant disease-related fungi.

For this purpose, the present disclosure provides the following technical solution:

A quinoline-2,3-fused nine-membered ring compound, structurally shown in Formula I:

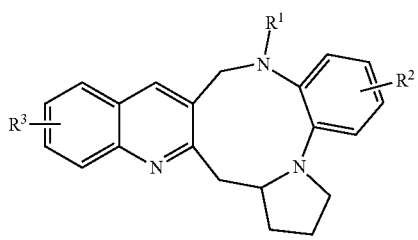

Formula I

Where:

R[1] is selected from benzyl, p-cyanobenzyl, p-trifluoromethylbenzyl, o-aldehydebenzyl, p-chlorobenzyl, m-methylbenzyl, 2-fluoro-4-chlorobenzyl, p-methoxybenzyl, furylmethyl, thenyl or menaphthyl;

R[2] is located at any feasible position of this benzene ring, and specifically selected from halogen, phenyl, methyl or methoxy;

R[3] is located at any feasible position of this benzene ring, and specifically selected from halogen, trifluoromethyl or methoxyl.

A preparation method of the quinoline-2,3-fused nine-membered ring compound includes the following steps:

mixing a quinoline-derived aniline compound and a formaldehyde compound, adding a solvent and a catalyst, controlling a system temperature, and reacting with stirring to obtain the quinoline-2,3-fused nine-membered ring compound.

In the above preparation method, the quinoline-derived aniline compound is selected from the structure shown in Formula II:

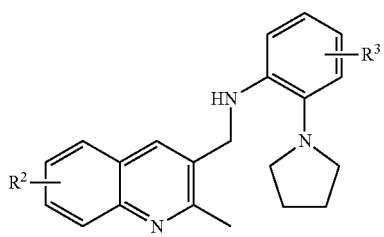

Formula II

Where:

R[2] is located at any feasible position of this benzene ring, and specifically selected from halogen, trichloromethylor, methoxy; and R[3] is located at any feasible position of this benzene ring, and specifically selected from halogen, phenyl, methyl or methoxy.

In the above preparation method, the formaldehyde compound is selected from the structure shown in Formula III:

R[1]—CHO   Formula III

Where:

R[1] is selected from phenyl, p-cyanophenyl, p-trifluoromethylphenyl, o-aldehydephenyl, p-chlorophenyl, m-methylphenyl, 2-fluoro-4-chlorophenyl, p-methoxyphenyl, furan, thiophene or naphthalene.

In the above preparation method, a molar ratio of the quinoline-derived aniline compound to the formaldehyde compound ranges from 1:1 to 1:4. In a specific implementation solution, the molar ratio of the quinoline-derived aniline compound to the formaldehyde compound is 1:3.

In the above preparation method, the solvent is selected from any one of 1,2-dichloroethane, ethyl alcohol, 1,4-dioxane, ethyl acetate, hexafluoroisopropanol, acetonitrile and N,N-dimethylformamide.

In the above preparation method, the catalyst is selected from any one of an acetic acid, a benzoic acid, a p-toluenesulfonic acid, a methanesulfonic acid, a trifluoromethanesulfonic acid, a camphorsulfonic acid, a trifluoroacetic acid, scandium trifluoromethanesulfonate and boron trifluoride diethyl etherate.

In the above preparation method, an amount of the catalyst ranges from 10 mol % to 100 mol %. In a specific implementation solution, the amount of the catalyst is 100 mol %.

In the above preparation method, the solvent is added in an amount of 10 L to 30 L per mole of a quinoline-derived o-phenylenediamine compound. In a specific implementation solution, the solvent is added in an amount of 30 L per mole of the quinoline-derived o-phenylenediamine compound.

In the above preparation method, a reaction temperature ranges from 50° C. to 70° C. In a specific implementation solution, the reaction temperature is 60° C.

The above reaction is conducted under hermetic conditions.

A molecular sieve is used for water removal in the above reaction, and may be selected from 3 Å MS, 4 Å MS or 5 Å MS.

In specific implementation solutions, the quinoline-2,3-fused nine-membered ring compound may be selected from the following specific structures:

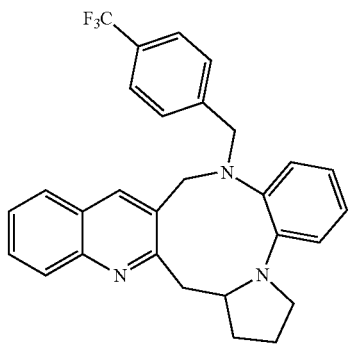

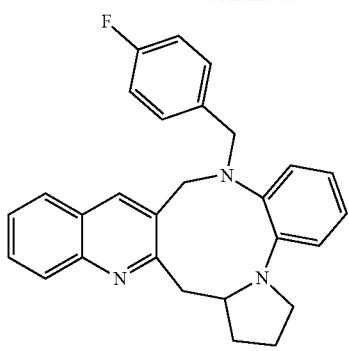

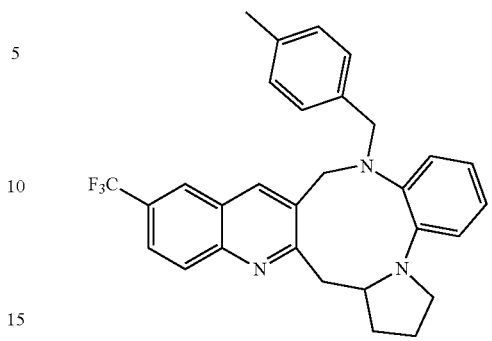

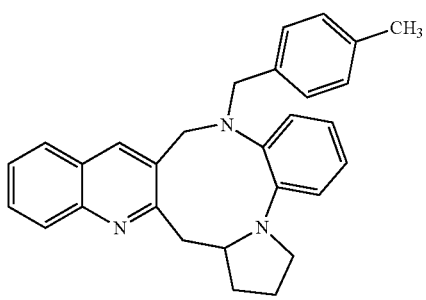

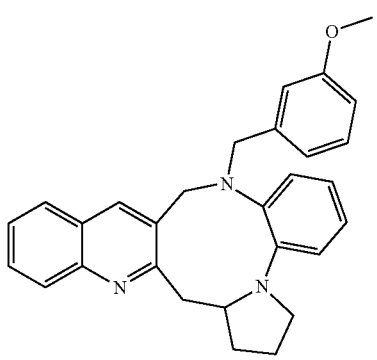

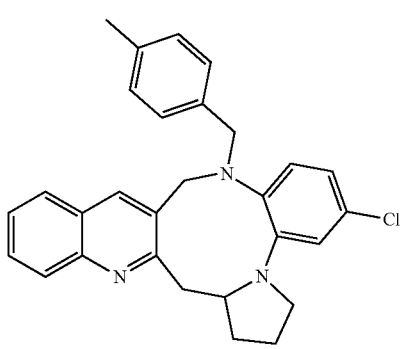

The present disclosure provides an application of the quinoline-2,3-fused nine-membered ring compound, which includes but is not limited to preparation into drugs or formulations having activities, such as anti-tumor, anti-mitosis, anti-HIV virus, anti-bacteria, enhanced mRNA expression of nerve growth factors and acetylcholinesterase inhibition.

In a specific application process, the above six quinoline-2,3-fused nine-membered ring compounds show an excellent inhibitory activity against plant disease-related fungi such as *C. gloeosporioides, V. mali, F. oxysporum, B. cinerea* and *G. graminis*.

The present disclosure provides a plant fungicide, and an effective component thereof is one or more of the quinoline-2,3-fused nine-membered ring compounds.

In the specific implementation solutions, the plant fungicide further includes pesticidally acceptable auxiliaries, additives, stabilizers, flavoring agents, emulsifiers or synergists.

In the specific implementation solutions, an effective concentration of the plant fungicide ranges from 25 mg/L to 100 mg/L. Preferably, the concentration is a total concentration of the effective component.

In the specific implementation solutions, a formulation of the plant fungicide is powder, a suspension agent, wettable powder, an emulsion, an emulsifiable solution cream, paste, a colloid, a fumigant, fumigant, a smoking generator, an aerosol, granules, fine granules or oil agents.

A reaction of N-((2-methylquinoline-3-yl)methyl-2-(pyrrolidine-1-yl)aniline with benzaldehyde is taken as an example to explain a reaction mechanism of the quinoline-derived aniline compound and the formaldehyde compound, shown as follows:

Benzaldehyde and compounds of quinoline amine derivatives are subjected to aldimine condensation under the promotion of an acid to generate positive iminium ions that trigger tetrahydropyrrole to generate 1,6-hydride transfer, and meanwhile a benzoic acid or hexafluoroisopropanol forms hydrogen bonds, which triggers quinoline dearomatization; and then quinoline methyl causes nucleophilic attack against imine, and aromatization is recovered to form nine-membered rings.

A simple reaction process is as follows:

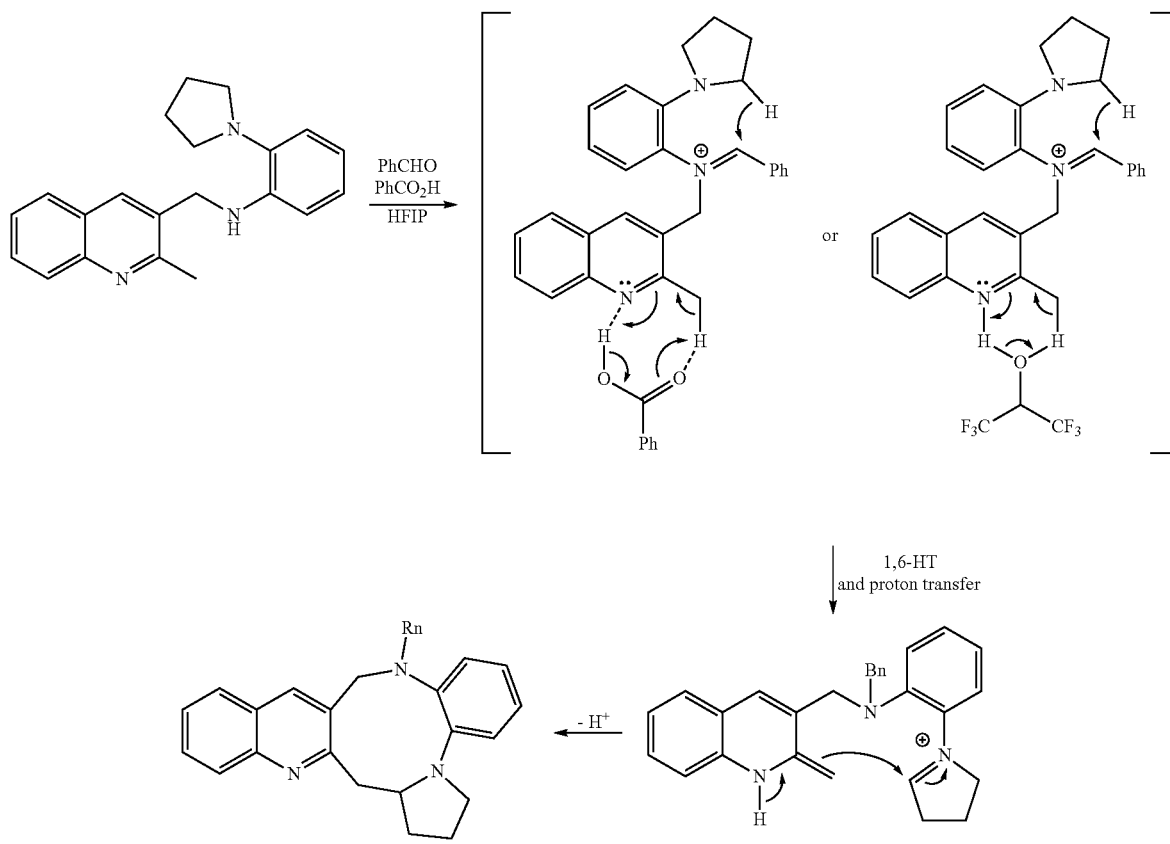

The present disclosure has the following beneficial effects:

According to the present disclosure, a 1,6-hydride transfer/cyclization strategy is triggered by aldimine condensation, the quinoline-derived aniline compound and the formaldehyde compound are prepared into the quinoline-2,3-fused nine-membered ring compound with a wide substrate scope and potential bioactivity by a one-pot synthesis method. The synthesis method in the present disclosure has the advantages of simple and available raw materials, high generality and applicability, mild reaction conditions, good chemoselectivity, high efficiency, environmental friendliness and the like. After tests on antibacterial activity of part of compounds, it is found that the quinoline-2,3-fused nine-membered ring compound shows an excellent inhibitory activity against five common agricultural pathogens: *G. graminis, C. gloeosporioides, B. cinerea, V. mali* and *F. oxysporum*.

BRIEF DESCRIPTION OF THE DRAWINGS

FIG. 1 shows inhibiting effects of six compounds on *G. graminis, C. gloeosporioides, B. cinerea, V. mali* and *F. oxysporum* at a concentration of 25 mg/L; in the FIGURE, a first column is pictures showing inhibitory effects of 5 pathogens in a control group; a second column is pictures showing inhibitory effect of a compound 1 on 5 pathogens; a third column is pictures showing inhibitory effect of a compound 2 on 5 pathogens; a fourth column is pictures showing inhibitory effect of a compound 3 on 5 pathogens; a fifth column is pictures showing inhibitory effect of a compound 4 on 5 pathogens; a sixth column is pictures showing inhibitory effect of a compound 5 on 5 pathogens; and a seventh column is pictures showing inhibitory effect of a compound 6 on 5 pathogens.

DETAILED DESCRIPTION OF THE EMBODIMENTS

Unless otherwise indicated, terms used in the present disclosure generally have the same meaning as commonly understood by those ordinarily skilled in the prior art. The present disclosure will be further described in detail with reference to the specific embodiments and data. The following embodiments are only used for illustrating the present disclosure rather than limiting the scope of the present disclosure in any form.

(I) Screening of Synthesis Conditions of Quinoline-2,3-Fused Nine-Membered Ring Compound 0.1 mmol of N-((2-methylquinoline-3-yl)methyl)-2-(pyrrolidine-1-yl)aniline and 0.2 mmol to 0.4 mmol of benzaldehyde were placed in a sealed tube, 1 mL to 3 mL of solvent, 0.01 mmol to 0.1 mmol of catalyst (10 mol % to 100 mol %) and 30 mg of molecular sieve (MS) moisture scavenger were added, and the mixture was stirred at 50° C. to 70° C. until completion of the reaction as indicated by TLC analysis. After completion of the reaction, separation and purification of a reactant were conducted by using a silica gel column, and rotary evaporation was conducted on the purified product to obtain a target product.

A chemical reaction formula is shown as follows:

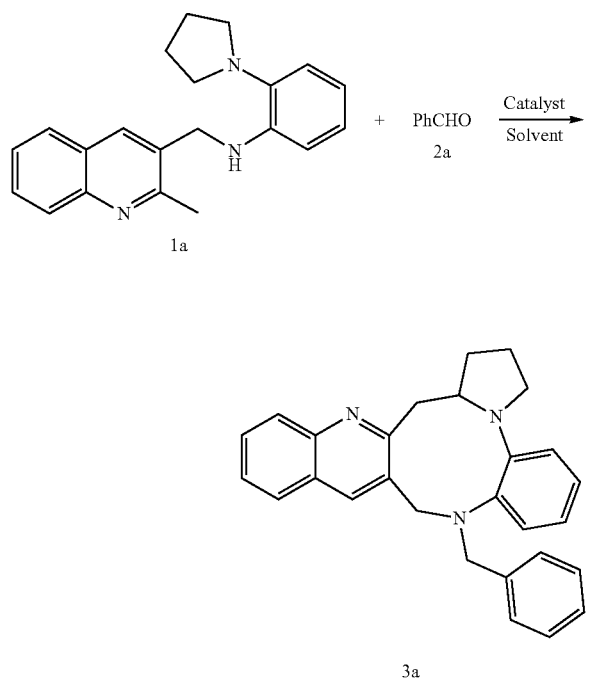

According to the above reaction process, parallel test groups were set, and different catalysts and solvents were used.

The catalysts include an acetic acid (AcOH), a benzoic acid (PhCO$_2$H), a p-toluenesulfonic acid (TsOH·H$_2$O), a methane sulfonic acid (MsOH), a trifluoromethanesulfonic acid (TfOH), a camphorsulfonic acid (CSA), a trifluoroacetic acid (TFA), scandium trifluoromethanesulfonate (Sc(OTf)$_3$) and boron trifluoride diethyl etherate (BF$_3$·OEt$_2$) respectively.

The solvents include 1,2-dichloroethane (DCE), ethyl alcohol (EtOH), 1,4-dioxane, ethyl acetate (EA), hexafluoroisopropanol (ITP), acetonitrile (CH$_3$CN) and N,N-dimethylformamide (DMF) respectively.

In a test process, it was found that a product was formed only under the condition of the hexafluoroisopropanol serving as the solvent. Therefore, the following conditions were screened by using the hexafluoroisopropanol.

The catalysts used in the test groups and the amounts thereof, amounts of substrates and test results were shown in Table 1:

TABLE 1

| Group | Catalyst | Amount of catalyst | Additive | Yield (%) |
|---|---|---|---|---|
| 1 | AcOH | 20 mol % | 3Å MS | 60 |
| 2 | PhCO$_2$H | 20 mol % | 3Å MS | 67 |
| 3 | TsOH•H$_2$O | 20 mol % | 3Å MS | 63 |
| 4 | MsOH | 20 mol % | 3Å MS | 55 |
| 5 | TfOH | 20 mol % | 3Å MS | 64 |
| 6 | (—)-CSA | 20 mol % | 3Å MS | 62 |
| 7 | TFA | 20 mol % | 3Å MS | 61 |
| 8 | Sc(OTf)$_3$ | 20 mol % | 3Å MS | 60 |
| 9 | BF$_3$•OEt$_2$ | 20 mol % | 3Å MS | 60 |
| 10 | PhCO$_2$H | 10 mol % | 3Å MS | 60 |
| 11 | PhCO$_2$H | 50 mol % | 3Å MS | 68 |
| 12 | PhCO$_2$H | 100 mol % | 3Å MS | 75 |

TABLE 1-continued

| Group | Catalyst | Amount of catalyst | Additive | Yield (%) |
|---|---|---|---|---|
| 13 | PhCO$_2$H | 100 mol % | — | 70 |
| 14 | PhCO$_2$H | 100 mol % | 4Å MS | 69 |
| 15 | PhCO$_2$H | 100 mol % | 5Å MS | 72 |
| 16 | PhCO$_2$H | 100 mol % | 3Å MS | 75 |
| 17 | PhCO$_2$H | 100 mol % | 3Å MS | 60 |
| 18 | PhCO$_2$H | 100 mol % | 3Å MS | 70 |
| 19 | PhCO$_2$H | 100 mol % | 3Å MS | 70 |

Note: In Table 1, the reaction of each group was conducted as follows without special statement: 0.1 mmol of N-((2-methylquinoline-3-yl)methyl)-2-(pyrrolidine-1-yl) aniline and 0.3 mmol of benzaldehyde, 0.02 mmol (20 mol %) of catalyst and 30 mg of 3 Å MS solution (MS) were added to 3 mL of ITP, and stirred at 60° C. for 48 hours. Wherein, in Group 16, the reaction was conducted with stirring at 50° C. for 4 days; in Group 17, a reaction temperature was 70° C.; in Group 18, an amount of the benzaldehyde was 0.2 mmol; and in Group 19, an amount of the benzaldehyde was 0.4 mmol.

According to the above test results, in line with the principle of green synthesis, reaction conditions of Group 12 were the optimal through screening: at 60° C., 0.1 mmol of quinoline-derived aniline compound and 0.3 mmol of formaldehyde compound served as reaction substrates, 3 mL of hexafluoroisopropanol was added as the solvent, the reaction substrates and the solvent were continuously stirred and reacted under the catalysis by 0.1 mmol of benzoic acid, till the raw materials reacted fully. The 3 Å molecular sieve was adopted for water removal in the reaction process.

All products in the following embodiments 1 to 31 were obtained through replacement of different reaction substrates based on the optimal reaction conditions in the above experimental solution. Wherein, the reaction substrates may be selected from the following structures:

(1) Quinoline-Derived Aniline Compound

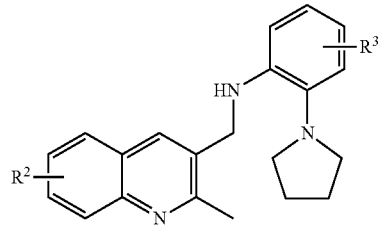

Where, R$^2$ is located at any feasible position of this benzene ring, and specifically selected from halogen, trichloromethylor, methoxy; and R$^3$ is located at any feasible position of this benzene ring, and specifically selected from halogen, phenyl, methyl or methoxy; and (2) Formaldehyde Compound

R$^1$—CHO

Where, R$^1$ is selected from benzyl, p-cyanobenzyl, p-trifluoromethylbenzyl, o-aldehydebenzyl, p-chlorobenzyl, m-methylbenzyl, 2-fluoro-4-chlorobenzyl, p-methoxybenzyl, furan, thiophene or naphthalene.

(II) Test on Antibacterial Activity of Quinoline-2,3-Fused Nine-Membered Ring Compound The following compounds were selected from the embodiments for test on the antibacterial activity:

1

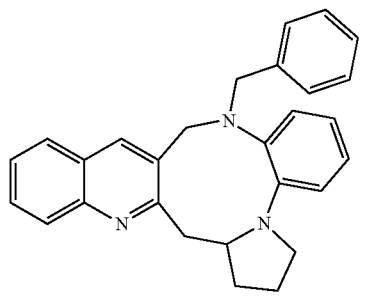

2

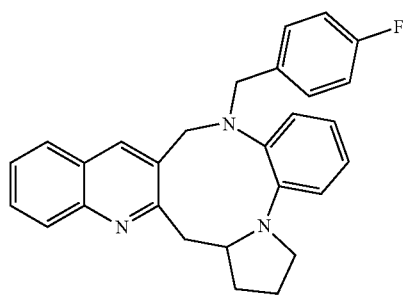

3

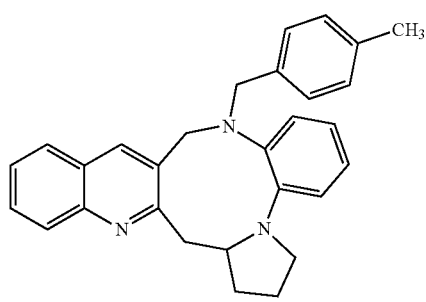

4

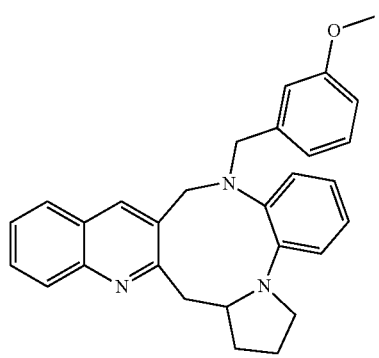

5

6

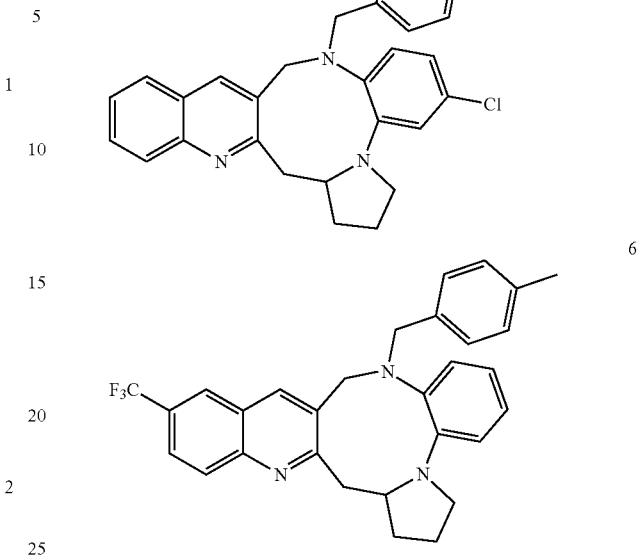

The test on the antibacterial activity was shown as follows:

Five common strains of C. gloeosporioides, V. mali, F. oxysporum, B. cinerea and G. graminis were selected, and the antibacterial activity of the compounds was tested by a mycelial growth rate method (Ann. Appl. Biol., 2008, 152, 369). The above strains for test were provided by Shangdong Biopesticide Engineering Research Center.

Firstly, a certain amount of potato dextrose agar (PDA) was weighed and placed in a wide neck flask, distilled water was added to the wide-necked flask, to prepare a culture medium, and the culture medium was placed in an autoclave for sterilization at 120° C. for half an hour. 1 mg of drugs to be tested were weighed and dissolved in 10 mL of acetone to prepare 100 mg/L of agents, a half of agents therein were taken and diluted with the acetone to 10 mL to prepare 50 mg/L of agents, and 25 mg/L, 12.5 mg/L and 6.25 mg/L of agents might be prepared in such way. 5 mL of agents therein were taken and poured into 50 mL of potato dextrose agar for uniform mixing, and then the mixtures were poured into 5 culture media sterilized at high temperature respectively. The five pathogens were inoculated with inoculation loops respectively after cooling, sealed with sealing films and transferred to a proper temperature for observation. When colonies in the control group without the agents reached 8000, the colonies in the experimental groups were measured by a cross intersection method according to the following formula:

Inhibition rate=(colony diameter of the control group−colony diameter of the experimental groups)/colony diameter of the control group× 1000

The test results were shown in Table 2:

TABLE 2

| Strains | Concentration | 1 | 2 | 3 | 4 | 5 | 6 |
|---|---|---|---|---|---|---|---|
| V. mali | 25 mg/L | 100 | 100 | 100 | 100 | 100 | 100 |
|  | 50 mg/L | 100 | 100 | 100 | 100 | 100 | 100 |
|  | 100 mg/L | 100 | 100 | 100 | 100 | 100 | 100 |

TABLE 2-continued

| Strains | Concentration | 1 | 2 | 3 | 4 | 5 | 6 |
|---|---|---|---|---|---|---|---|
| C. gloeos- | 25 mg/L | 100 | 92.4 | 100 | 100 | 88.1 | 74.6 |
| porioides | 50 mg/L | 100 | 100 | 100 | 100 | 100 | 82.1 |
|  | 100 mg/L | 100 | 100 | 100 | 100 | 100 | 100 |
| G. graminis | 25 mg/L | 36.9 | 100 | 58.2 | 61.2 | 35.9 | 56.3 |
|  | 50 mg/L | 54.1 | 100 | 62.1 | 66.5 | 51.9 | 100 |
|  | 100 mg/L | 68.9 | 100 | 100 | 100 | 75.1 | 100 |
| B. cinerea | 25 mg/L | 100 | 100 | 100 | 100 | 100 | 100 |
|  | 50 mg/L | 100 | 100 | 100 | 100 | 100 | 100 |
|  | 100 mg/L | 100 | 100 | 100 | 100 | 100 | 100 |
| F. oxysporum | 25 mg/L | 49.3 | 100 | 100 | 100 | 100 | 86.5 |
|  | 50 mg/L | 100 | 100 | 100 | 100 | 100 | 100 |
|  | 100 mg/L | 100 | 100 | 100 | 100 | 100 | 100 |

It can be known from Table 2 that the quinoline-2,3-fused nine-membered ring compound synthesized in the present disclosure showed an excellent inhibitory activity against *C. gloeosporioides*, *V. mali*, *F. oxysporum*, *B. cinerea* and *G. graminis*. 1711 The present disclosure provides pictures showing inhibitory effects of the above compounds against *G. graminis*, *C. gloeosporioides*, *B. cinerea*, *V. mali* and *F. oxysporum* at a concentration of 25 mg/L, as shown in FIG. 1. Wherein, the compounds 1 to 6 may show an excellent inhibitory activity against *C. gloeosporioides*, *V. mali*, *F. oxysporum*, *B. cinerea* and *G. graminis* at the low concentration of 25 mg/L, and especially for *V. mali* and *B. cinerea*, the antibacterial rate of the compounds is up to 100%. Comparatively, a higher compound concentration is required for inhibition on *G. graminis*, and the prevention and control effect on *G. graminis* is slightly inferior to that on other pathogens.

In conclusion, in a practical application process, the quinoline-2,3-fused nine-membered ring compound may be used for preparing bactericidal drugs, or serve as a lead compound for sterilization after modification.

The structures and nuclear magnetic resonance data of the reaction products in the embodiments 1 to 31 are shown as follows:

Embodiment 1

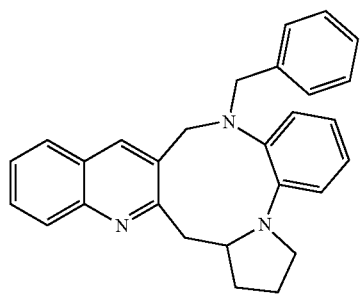

9-benzyl-2,3,9,10,17,17a-hexahydro-1H-benzo[2,3]pyrrolo[1',2':1,9][1,4]diazonino[7,6-b]quinolone: According to general procedure (for 48 h), quinolines (63.5 mg, 0.2 mmol), aldehydes (63.7 mg, 0.6 mmol), PhCO$_2$H (24.4 mg, 0.2 mmol), afforded (56 mg, 69%) as a yellow oil after purification on silica gel (petroleum ether/EtOAc=50:1). $^1$H NMR (500 MHz, CDCl$_3$) δ 8.02 (d, J=8.5 Hz, 1H), 7.69-7.67 (m, 2H), 7.64-7.61 (m, 1H), 7.45-7.42 (m, 1H), 7.32-7.29 (m, 2H), 7.24 (d, J=1.5 Hz, 1H), 7.21-7.19 (m, 2H), 7.04 (dd, J=7.5, 1.5 Hz, 1H), 6.74-6.70 (m, 1H), 6.72 (td, J=7.5, 1.5 Hz, 1H), 6.64 (dd, J=8.5, 1.5 Hz, 1H), 4.56 (d, J=14.5 Hz, 1H), 4.52-4.42 (m, 1H), 4.35 (d, J=14.0 Hz, 1H), 4.12-4.06 (m, 2H), 3.31 (dd, J=12.5, 6.5 Hz, 1H), 3.17-3.13 (m, 2H), 3.06-3.02 (m, 1H), 2.17-2.12 (m, 1H), 2.08-1.97 (m, 2H), 1.86-1.79 (m, 1H). $^{13}$C NMR (126 MHz, CDCl$_3$) δ 162.17, 146.99, 143.26, 139.67, 137.73, 135.15, 131.81, 129.47 (s, 2C), 128.74, 128.53, 128.24 (s, 2C), 127.14, 127.12, 126.99, 125.83, 125.73, 125.18, 118.55, 116.93, 61.33, 58.17 57.99, 50.32, 43.17, 34.48, 23.22. HRMS (ESI-TOF): m/z [M+H]+ calcd for C$_{28}$H$_{27}$N$_3$: 406.2277, found: 406.2280.

Embodiment 2

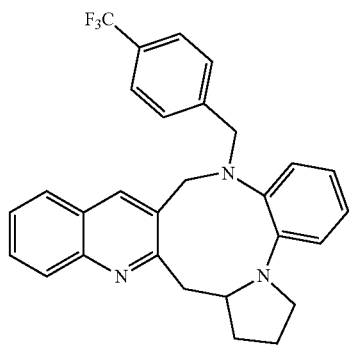

9-(4-(trifluoromethyl)benzyl)-2,3,9,10,17,17a-hexahydro-1H-benzo[2,3]pyrrolo[1',2':1,9][1,4]diazonino[7,6-b]quinolone: According to general procedure (for 48 h), quinolines (63.5 mg, 0.2 mmol), aldehydes (104.5 mg, 0.6 mmol), PhCO$_2$H (24.4 mg, 0.2 mmol), afforded (49.4 mg, 46%) as a white oil after purification on silica gel (petroleum ether/EtOAc=50:1). $^1$H NMR (500 MHz, CDCl$_3$) δ 8.03 (d, J=8.5 Hz, 1H), 7.72 (s, 1H), 7.70 (d, J=8.0 Hz, 1H), 7.64 (t, J=8.0 Hz, 1H), 7.53 (d, J=8.0 Hz, 2H), 7.46 (t, J=8.0 Hz, 1H), 7.26 (d, J=8.0 Hz, 2H), 6.99 (t, J=8.0 Hz, 2H), 6.74 (t, J=8.0 Hz, 1H), 6.70 (d, J=8.0 Hz, 1H), 4.67 (d, J=14.0 Hz, 1H), 4.36-4.34 (m, 1H), 4.30 (d, J=14.5 Hz, 1H), 4.11 (q, 14.0 Hz, 2H), 3.26-3.22 (m, 1H), 3.21-3.17 (m, 1H), 3.16-3.09 (m, 2H), 2.22-2.15 (m, 1H), 2.04-1.95 (m, 2H), 1.83-1.76 (m, 1H). $^{13}$C NMR (126 MHz, CDCl$_3$) δ 162.02, 147.10, 143.26, 141.82, 139.24, 135.14, 131.51, 129.60 (s, 2C), 129.37 (q, J=32.4 Hz, 1C), 128.91, 128.66, 127.14, 126.96, 125.90, 125.51, 125.12 (q, J=3.9 Hz, 2C), 124.24 (q, J=253.1 Hz, 1C), 118.87, 117.43, 61.54, 58.29, 57.32, 50.42, 42.97, 34.36, 23.29. $^{19}$FNMR (470 MHz, CDCl$_3$) δ -62.36. HRMS (ESI-TOF): m/z [M+H]+ calcd for C$_{29}$H$_{26}$F$_3$N$_3$: 474.2151, found: 474.2152.

Embodiment 3

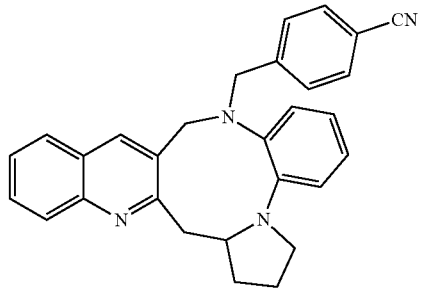

4-((1,2,3,10,17,17a-hexahydro-9H-benzo[2,3]pyrrolo[1',2':1,9][1,4]diazonino[7,6-b]quinolin-9-yl)methyl)benzonitrile: According to general procedure (for 48 h), quinolines (63.5 mg, 0.2 mmol), aldehydes (78.7 mg, 0.6 mmol), PhCO$_2$H (24.4 mg, 0.2 mmol), afforded (24 mg, 28%) as a white oil after purification on silica gel (petroleum ether/EtOAc=100:1). $^1$H NMR (500 MHz, CDCl$_3$) δ 8.04 (d, J=8.5 Hz, 1H), 7.75 (s, 1H), 7.72 (d, J=8.0 Hz, 1H), 7.66 (t, J=7.5 Hz, 1H), 7.56 (d, J=9.0 Hz, 2H), 7.48 (t, J=8.0 Hz, 1H), 7.23 (d, J=8.0 Hz, 2H), 7.02-6.94 (m, 2H), 6.77-6.67 (m, 2H), 4.70 (d, J=14.5 Hz, 1H), 4.36-4.24 (m, 2H), 4.10 (dd, J=14.5 Hz, 2H), 3.25-3.18 (m, 2H), 3.14 (t, J=6.5 Hz, 2H), 2.31-2.09 (m, 1H), 2.05-1.94 (m, 2H), 1.84-1.75 (m, 1H). $^{13}$C NMR (126 MHz, CDCl$_3$) δ 161.93, 147.10, 143.28, 143.24, 138.81, 135.13, 131.96 (s, 2C), 131.30, 129.95 (s, 2C), 128.98, 128.66, 127.11, 126.92, 126.01, 125.97, 125.71, 118.88, 118.86, 117.51, 110.94, 61.55, 58.47, 57.35, 50.41, 42.86, 34.32, 29.70, 23.27. HRMS (ESI-TOF): m/z [M+H]$^+$ calcd for C$_{29}$H$_{26}$N$_4$: 431.2230, found: 431.2229.

Embodiment 4

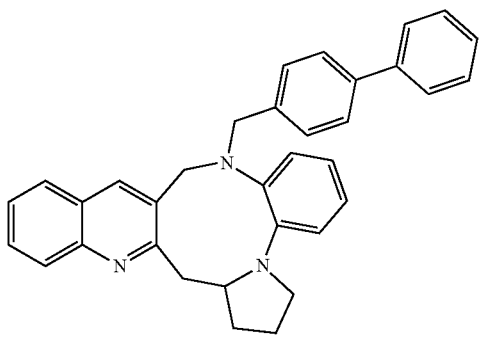

9-([1,1'-biphenyl]-4-ylmethyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (109.3 mg, 0.6 mmol), PhCO$_2$H (24.4 mg, 0.2 mmol), afforded (52.9 mg, 55%) as a white oil after purification on silica gel (petroleum ether/EtOAc=30:1). $^1$H NMR (500 MHz, CDCl$_3$) δ 8.02 (d, J=8.0 Hz, 1H), 7.70 (s, 1H), 7.67 (dd, J=8.5, 1.5 Hz, 1H), 7.62 (ddd, J=8.5, 6.5, 1.5 Hz, 1H), 7.58-7.54 (m, 2H), 7.54-7.48 (m, 2H), 7.45-7.38 (m, 3H), 7.36-7.31 (m, 1H), 7.28-7.23 (m, 2H), 7.08 (dd, J=7.5, 1.5 Hz, 1H), 6.97 (td, J=8.5, 7.5, 2.0 Hz, 1H), 6.74 (td, J=7.5, 1.5 Hz, 1H), 6.66 (dd, J=8.5, 1.5 Hz, 1H), 4.60 (d, J=14.0 Hz, 1H), 4.55-4.47 (m, 1H), 4.38 (d, J=14.0 Hz, 1H), 4.13 (dd, J=14.0 Hz, 2H), 3.34 (dd, J=13.0, 6.5 Hz, 1H), 3.21-3.11 (m, 2H), 3.10-3.00 (m, 1H), 2.23-2.11 (m, 1H), 2.09-1.97 (m, 2H), 1.89-1.76 (m, 1H). $^{13}$C NMR (126 MHz, CDCl$_3$) δ 162.14, 147.02, 143.24, 140.84, 139.98, 139.69, 136.78, 135.06, 131.81, 129.87 (s, 2C), 128.74 (s, 2C), 128.69, 128.57, 127.21, 127.12, 127.04 (s, 2C), 126.96, 126.91 (s, 2C), 125.81, 125.71, 125.20, 118.60, 117.00, 61.36, 58.24, 57.68, 50.32, 43.18, 34.44, 23.21. HRMS (ESI-TOF): m/z [M+H]+ calcd for C$_{34}$H$_{31}$N$_3$: 482.2590, found: 482.2590.

Embodiment 5

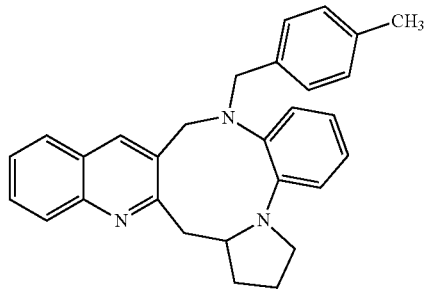

9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (72.1 mg, 0.6 mmol), PhCO$_2$H (24.4 mg, 0.2 mmol), afforded (63.2 mg, 77%) as a white oil after purification on silica gel (petroleum ether/EtOAc=100:1). $^1$H NMR (500 MHz, CDCl$_3$) δ 8.01 (d, J=8.5 Hz, 1H), 7.66 (d, J=5.0 Hz, 2H), 7.61 (t, J=7.5 Hz, 1H), 7.42 (t, J=7.5 Hz, 1H), 7.10 (s, 4H), 7.04 (d, J=8.0 Hz, 1H), 6.94 (t, J=7.5 Hz, 1H), 6.71 (t, J=7.5 Hz, 1H), 6.63 (d, J=8.0 Hz, 1H), 4.60-4.43 (m, 2H), 4.34 (d, J=14.0 Hz, 1H), 4.13-4.00 (m, 2H), 3.33 (dd, J=13.0, 6.5 Hz, 1H), 3.21-3.09 (m, 2H), 3.07-2.98 (m, 1H), 2.32 (s, 3H), 2.19-2.10 (m, 1H), 2.09-1.96 (m, 2H), 1.88-1.77 (m, 1H). $^{13}$C NMR (126 MHz, CDCl$_3$) δ 161.11, 145.93, 142.19, 138.66, 135.64, 134.02, 133.61, 130.79, 128.38 (s, 2C), 127.87 (s, 2C), 127.60, 127.48, 126.06, 125.91, 124.71, 124.60, 124.07, 117.39, 115.71, 60.18, 57.05, 56.68, 49.22, 42.23, 33.47, 22.12, 20.08. HRMS (ESI-TOF): m/z [M+H]+ calcd for C$_{29}$H$_{29}$N$_3$: 420.2434, found: 420.2433.

Embodiment 6

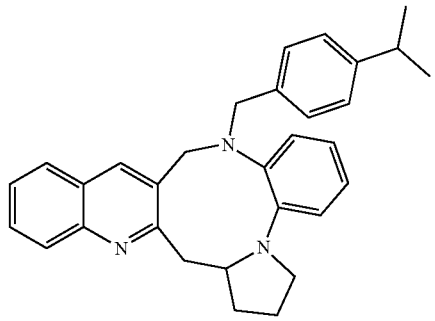

9-(4-isopropylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (88.9 mg, 0.6 mmol), PhCO$_2$H (24.4 mg, 0.2 mmol), afforded (55.4 mg, 62%) as a white oil after purification on silica gel (petroleum ether/EtOAc=50:1). $^1$H NMR (500 MHz, CDCl$_3$) δ 7.21-7.05 (m, 8H), 7.01 (dd, J=7.5, 1.5 Hz, 1H), 6.92 (td, J=8.0, 1.5 Hz, 1H), 6.88 (d, J=7.5 Hz, 1H), 6.60 (s, 1H), 6.57 (t, J=7.5 Hz, 1H), 6.23 (d, J=7.5 Hz, 1H), 6.18 (s, 1H), 5.73 (dd, J=8.0, 1.0 Hz, 2H), 5.23 (s, 1H), 4.42 (s, 2H), 4.30 (s, 1H), 3.24 (dd, J=102.5, 16.0 Hz, 2H). $^{13}$C NMR (126 MHz, CDCl$_3$) δ 161.12, 146.65, 145.94, 142.20, 138.96, 134.03, 133.99, 130.91, 128.38 (s, 2C), 127.59, 127.51, 126.07, 125.91, 125.20 (s, 2C), 124.60, 124.00, 117.55, 115.89, 60.32, 57.17, 56.82, 49.28, 42.18, 33.41, 32.74, 28.68, 22.98, 22.18. HRMS (ESI-TOF): m/z [M+H]+ calcd for $C_{31}H_{33}N_3$: 448.2747, found: 448.2745.

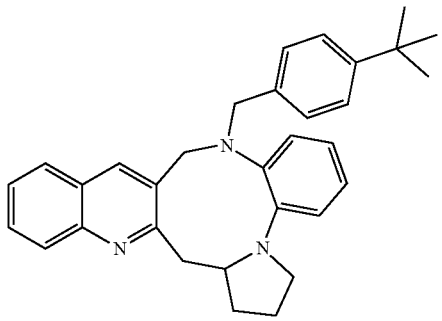

Embodiment 7

9-(4-(tert-butyl)benzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (97.3 mg, 0.6 mmol), $PhCO_2H$ (24.4 mg, 0.2 mmol), afforded (41.6 mg, 45%) as a white oil after purification on silica gel (petroleum ether/EtOAc=50:1). $^1H$ NMR (500 MHz, $CDCl_3$) δ 8.01 (d, J=8.5 Hz, 1H), 7.65 (d, J=3.4 Hz, 2H), 7.60 (t, J=7.0 Hz, 1H), 7.41 (d, J=8.0 Hz, 1H), 7.30 (d, J=8.0 Hz, 2H), 7.13 (d, J=8.0 Hz, 2H), 7.08 (d, J=7.5 Hz, 1H), 6.95 (d, J=8.0 Hz, 1H), 6.74 (d, J=8.0 Hz, 1H), 6.65 (d, J=7.5 Hz, 1H), 4.55 (d, J=14.0 Hz, 1H), 4.53-4.46 (m, 1H), 4.35 (d, J=14.0 Hz, 1H), 4.08 (s, 2H), 3.36 (t, J=13.0, 6.5 Hz, 1H), 3.20-3.08 (m, 2H), 3.06-2.98 (m, 1H), 2.22-2.09 (m, 1H), 2.07-1.93 (m, 2H), 1.80 (qd, J=9.5, 8.5, 4.9 Hz, 1H), 1.29 (s, 9H). $^{13}C$ NMR (126 MHz, $CDCl_3$) δ 162.13, 149.93, 146.96, 143.20, 140.10, 135.01, 134.69, 131.97, 129.12 (s, 2C), 128.60, 128.53, 127.10, 126.93, 125.62, 125.55, 125.06 (s, 2C), 124.99, 118.64, 116.98, 61.39, 58.23, 57.76, 50.32, 43.19, 34.46, 34.39, 31.36 (s, 2C), 26.91, 23.22. HRMS (ESI-TOF): m/z [M+H]+ calcd for $C_{32}H_{35}N_3$: 462.2903, found: 462.2903.

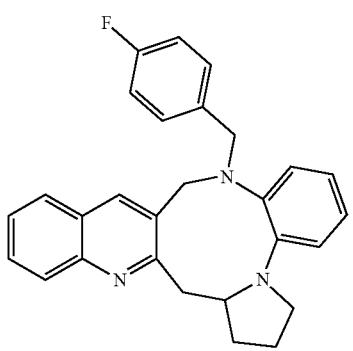

Embodiment 8

9-(4-fluorobenzyl)-2,3,9,10,17,17a-hexahydro-1H-benzo[2,3]pyrrolo[1',2':1,9][1,4]diazonino[7,6-b]quinolone: According to general procedure (for 48 h), quinolines (63.5 mg, 0.2 mmol), aldehydes (74.5 mg, 0.6 mmol), $PhCO_2H$ (24.4 mg, 0.2 mmol), afforded (49.4 mg, 58%) as a white oil after purification on silica gel (petroleum ether/EtOAc=50:1). $^1H$ NMR (500 MHz, $CDCl_3$) δ 8.02 (d, J=8.5 Hz, 1H), 7.69 (d, J=8.5 Hz, 2H), 7.63 (t, J=7.5 Hz, 1H), 7.45 (t, J=7.5 Hz, 1H), 7.11 (t, J=7.0 Hz, 2H), 7.02 (d, J=7.5 Hz, 1H), 6.96 (t, J=8.0 Hz, 3H), 6.71 (t, J=7.5 Hz, 1H), 6.62 (d, J=8.0 Hz, 1H), 4.51 (d, J=14.0 Hz, 1H), 4.53-4.45 (m, 1H), 4.31 (d, J=14.5 Hz, 1H), 4.03 (t, J=14.5 Hz, 2H), 3.23 (dd, J=13.0, 6.5 Hz, 1H), 3.18-3.11 (m, 2H), 3.07 (q, J=12.5, 5.5 Hz, 1H), 2.16 (p, J=18.5, 7.5 Hz, 1H), 2.09-1.98 (m, 2H), 1.86-1.77 (m, 1H). $^{13}C$ NMR (126 MHz, $CDCl_3$) δ 163.04, 162.19, 161.09, 147.09, 143.50, 138.98, 134.98, 133.43 (d, J=3.4 Hz, 1C), 131.70, 131.07 (d, J=8.0 Hz, 1C), 128.79, 128.63, 127.14, 126.98, 126.28, 125.80, 125.59, 118.32, 116.78, 115.07, 114.90, 61.13, 58.35, 57.33, 50.27, 43.23, 34.67, 23.17. $^{19}F$ NMR (470 MHz, $CDCl_3$) δ −115.67. HRMS (ESI-TOF): m/z [M+H]+ calcd for $C_{28}H_{26}FN_3$: 424.2183, found: 424.2184.

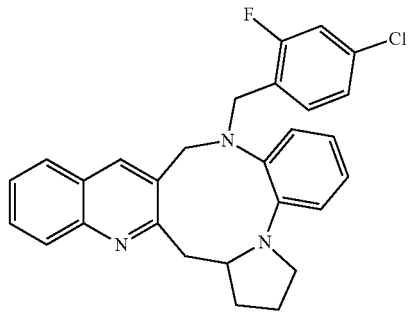

Embodiment 9

9-(4-chloro-2-fluorobenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (95.1 mg, 0.6 mmol), $PhCO_2H$ (24.4 mg, 0.2 mmol), afforded (36.6 mg, 40%) as a white oil after purification on silica gel (petroleum ether/EtOAc=100:1). $^1H$ NMR (500 MHz, $CDCl_3$) δ 8.02 (d, J=8.5 Hz, 1H), 7.77 (s, 1H), 7.72 (dd, J=8.5, 1.5 Hz, 1H), 7.64 (ddd, J=8.5, 7.0, 1.5 Hz, 1H), 7.46 (ddd, J=8.0, 7.0, 1.0 Hz, 1H), 7.23 (dd, J=9.5, 2.0 Hz, 1H), 7.15 (dd, J=8.5, 2.0 Hz, 1H), 6.99 (ddd, J=8.5, 7.0, 1.5 Hz, 1H), 6.94 (dd, J=8.0, 2.0 Hz, 1H), 6.89 (t, J=8.0 Hz, 1H), 6.68 (ddd, J=8.5, 7.0, 1.0 Hz, 1H), 6.63 (dd, J=8.0, 1.5 Hz, 1H), 4.51 (d, J=14.5 Hz, 1H), 4.42-4.37 (m, 1H), 4.35 (d, J=14.5 Hz, 1H), 4.08 (dd, J=14.5, 1.5 Hz, 1H), 3.96 (d, J=14.0 Hz, 1H), 3.24-3.08 (m, 4H), 2.25-2.15 (m, 1H), 2.12-2.00 (m, 2H), 1.89-1.79 (m, 1H). $^{13}C$ NMR (126 MHz, $CDCl_3$) δ 162.22 (d, 6.3 Hz, 1C), 160.21, 147.12, 143.58, 137.78, 135.08, 133.28 (d, 5.4 Hz, 1C), 131.43, 128.81, 128.62, 127.23, 127.06, 127.02 (d, 2.5 Hz, 1C), 126.03, 125.79, 123.78 (d, 16.6 Hz, 1C), 121.24 (d, 9.5 Hz, 1C), 119.05, 118.84, 117.98, 116.52, 60.86, 58.56, 50.19, 50.08, 43.24, 34.85, 23.15. HRMS (ESI-TOF): m/z [M+H]+ calcd for $C_{28}H_{25}FN_3$: 458.1793, found: 458.1795.

Embodiment 10

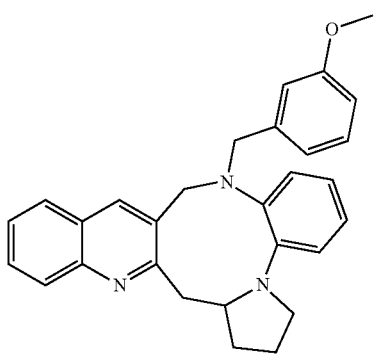

9-(3-methoxybenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (81.7 mg, 0.6 mmol), PhCO$_2$H (24.4 mg, 0.2 mmol), afforded (43.2 mg, 50%) as a white oil after purification on silica gel (petroleum ether/EtOAc=100:1). $^1$H NMR (500 MHz, CDCl$_3$) δ 8.01 (d, J=8.5 Hz, 1H), 7.70-7.67 (m, 2H), 7.62 (t, J=7.5 Hz, 1H), 7.44 (t, J=8.0 Hz, 1H), 7.22 (t, J=8.0 Hz, 1H), 7.05 (d, J=8.0 Hz, 1H), 6.95 (t, J=8.0 Hz, 1H), 6.80 (t, J=8.0 Hz, 2H), 6.74-6.71 (m, 2H), 6.65 (d, J=8.0 Hz, 1H), 4.57 (d, J=14.0 Hz, 1H), 4.49 (qd, J=7.0, 4.0 Hz, 1H), 4.35 (s, 1H), 4.09-4.03 (m, 2H), 3.73 (s, 3H), 3.32 (dd, J=13.0, 6.5 Hz, 1H), 3.19-3.14 (m, 2H), 3.08-3.04 (m, 1H), 2.20-2.12 (m, 1H), 2.08-1.97 (m, 2H), 1.85-1.81 (m, 1H). $^{13}$C NMR (126 MHz, CDCl$_3$) δ 162.11, 159.52, 147.00, 143.19, 139.68, 139.37, 135.14, 131.77, 129.18, 128.71, 128.54, 127.12, 126.96, 125.83, 125.71, 125.17, 121.72, 118.56, 116.95, 114.71, 112.81, 61.31, 58.17, 57.94, 55.12, 50.31, 43.15, 34.40, 23.19. HRMS (ESI-TOF): m/z [M+H]+ calcd for C$_{29}$H$_{29}$N$_3$O: 436.2383, found: 436.2383.

Embodiment 11

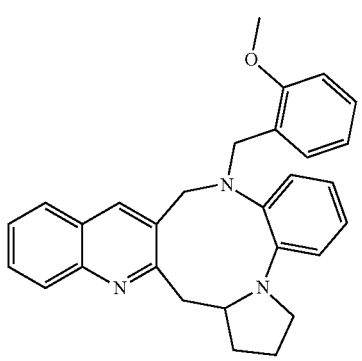

9-(2-methoxybenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (81.7 mg, 0.6 mmol), PhCO$_2$H (24.4 mg, 0.2 mmol), afforded (46.3 mg, 53%) as a white oil after purification on silica gel (petroleum ether/EtOAc=50:1). $^1$H NMR (500 MHz, CDCl$_3$) δ 8.01 (d, J=8.5 Hz, 1H), 7.64 (d, J=8.0 Hz, 2H), 7.60 (t, J=7.0 Hz, 1H), 7.41 (t, J=7.5 Hz, 1H), 7.21 (t, J=8.5 Hz, 1H), 7.08 (dd, J=15.5, 7.5 Hz, 2H), 6.91 (t, J=7.5 Hz, 1H), 6.86 (t, J=7.5 Hz, 1H), 6.80 (d, J=8.5 Hz, 1H), 6.72 (t, J=7.5 Hz, 1H), 6.65 (d, J=8.0 Hz, 1H), 4.67 (d, J=14.5 Hz, 1H), 4.49 (tt, J=6.5, 3.0 Hz, 1H), 4.38 (d, J=14.0 Hz, 1H), 4.17 (dd, 20.5, 14.0 Hz, 2H), 3.63 (d, 15 Hz, 3H), 3.42 (dd, J=13.0, 6.5 Hz, 1H), 3.13 (q, J=8.0 Hz, 1H), 3.08-3.03 (m, 1H), 3.00-2.95 (m, 1H), 2.09-2.02 (m, 1H), 1.99-1.92 (m, 2H), 1.82-1.76 (m, 1H). $^{13}$C NMR (126 MHz, CDCl$_3$) δ 162.25, 157.85, 146.89, 142.86, 140.29, 135.07, 132.24, 131.01, 128.51, 128.46, 128.39, 127.07, 126.96, 125.84, 125.54, 124.78, 124.44, 120.01, 118.83, 117.04, 110.05, 61.44, 58.55, 54.81, 52.02, 50.19, 43.07, 33.90, 23.21. HRMS (ESI-TOF): m/z [M+H]+ calcd for C$_{29}$H$_{29}$N$_3$O: 436.2383, found: 436.2383.

Embodiment 12

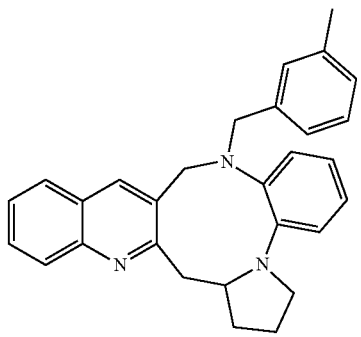

9-(3-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (72.1 mg, 0.6 mmol), PhCO$_2$H (24.4 mg, 0.2 mmol), afforded (40 mg, 49%) as a white oil after purification on silica gel (petroleum ether/EtOAc=50:1). $^1$H NMR (500 MHz, CDCl$_3$) δ 8.01 (d, J=8.5 Hz, 1H), 7.67 (d, J=7.5 Hz, 2H), 7.62 (d, J=7.5 Hz, 1H), 7.43 (d, J=7.5 Hz, 1H), 7.22-7.16 (m, 1H), 7.08-7.00 (m, 4H), 6.94 (d, J=7.5 Hz, 1H), 6.73 (d, J=7.5 Hz, 1H), 6.66 (d, J=8.0 Hz, 1H), 4.59 (d, J=14.5 Hz, 1H), 4.49 (qt, J=7.5, 3.0 Hz, 1H), 4.35 (dd, J=14.5, 2.5 Hz, 1H), 4.12-4.02 (m, 2H), 3.35 (dd, J=13.0, 6.5 Hz, 1H), 3.19-3.09 (m, 2H), 3.07-2.99 (m, 1H), 2.31 (s, 3H), 2.19-2.10 (m, 1H), 2.07-1.94 (m, 2H), 1.88-1.79 (m, 2H). $^{13}$C NMR (126 MHz, CDCl$_3$) 13C NMR (126 MHz, Chloroform-d) δ 162.09, 146.98, 143.10, 140.04, 137.77, 137.68, 135.13, 131.84, 130.15, 128.66, 128.53, 128.11, 127.78, 127.09, 126.95, 126.38, 125.66, 125.48, 124.93, 118.73, 117.07, 61.50, 58.09, 57.91, 50.34, 43.11, 34.24, 23.22, 21.43. HRMS (ESI-TOF): m/z [M+H]+ calcd for C$_{29}$H$_{29}$N$_3$: 420.2434, found: 420.2434.

Embodiment 13

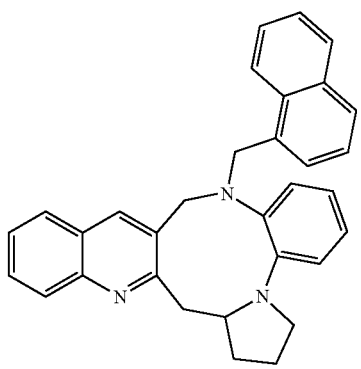

9-(naphthalen-1-ylmethyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (93.7 mg, 0.6 mmol), PhCO$_2$H (24.4 mg, 0.2 mmol), afforded (41.2 mg, 46%) as a white oil after purification on silica gel (petroleum ether/EtOAc=50:1). $^1$H NMR (500 MHz, CDCl$_3$) δ 8.00 (d, J=8.5 Hz, 1H), 7.82 (t, J=9.0 Hz, 2H), 7.76 (d, J=8.0 Hz, 1H), 7.70 (s, 1H), 7.68-7.60 (m, 2H), 7.45-7.39 (m, 3H), 7.35 (d, J=7.0 Hz, 1H), 7.31 (t, J=7.5 Hz, 1H), 7.05 (d, J=8.0 Hz, 1H), 6.93 (t, J=7.5 Hz, 1H), 6.82-6.72 (m, 2H), 5.00 (d, J=14.5 Hz, 1H), 4.68 (d, J=15.0 Hz, 1H), 4.59 (d, J=14.5 Hz, 1H), 4.44 (d, J=14.5 Hz, 1H), 4.17 (s, 1H), 3.33 (dd, J=13.0, 5.5 Hz, 1H), 3.12 (q, J=9.0 Hz, 2H), 3.06-3.02 (m, 1H), 2.01-1.93 (m, 1H), 1.85-1.76 (m, 2H), 1.70-1.64 (m, 2H). $^{13}$C NMR (126 MHz, CDCl$_3$) δ 161.90, 146.98, 142.77, 141.69, 135.56, 133.91, 133.04, 132.15, 132.00, 128.77, 128.56, 128.54, 127.89, 127.12 (s, 2C), 126.93, 125.76, 125.65, 125.58, 125.16, 124.23, 124.17, 123.97, 120.28, 118.74, 62.71, 58.30, 54.96, 50.84, 42.46, 33.08, 23.38. HRMS (ESI-TOF): m/z [M+H]+ calcd for C$_{32}$H$_{29}$N$_3$: 456.2434, found: 456.2434.

Embodiment 14

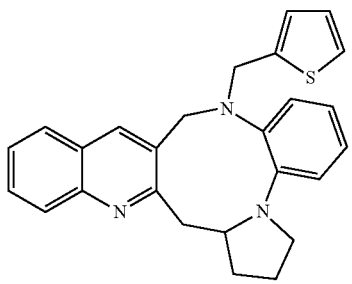

9-(thiophen-2-ylmethyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (67.3 mg, 0.6 mmol), PhCO$_2$H (24.4 mg, 0.2 mmol), afforded (6.6 mg, 8%) as a white oil after purification on silica gel (petroleum ether/EtOAc=100:1). $^1$H NMR (500 MHz, CDCl$_3$) δ 8.01 (d, J=8.5 Hz, 1H), 7.68 (d, J=10.5 Hz, 2H), 7.62 (t, J=7.5 Hz, 1H), 7.44 (t, J=7.5 Hz, 1H), 7.22 (t, J=4.5 Hz, 1H), 7.09 (d, J=8.0 Hz, 1H), 7.01-6.92 (m, 2H), 6.88 (s, 1H), 6.67 (t, J=7.5 Hz, 1H), 6.53 (d, J=8.0 Hz, 1H), 4.70 (s, 1H), 4.48 (d, J=14.0 Hz, 1H), 4.28 (d, J=14.0 Hz, 1H), 4.25-4.18 (m, 2H), 3.31 (dd, J=12.5, 7.0 Hz, 1H), 3.24-3.13 (m, 2H), 3.12-3.00 (m, 1H), 2.23-2.12 (m, 2H), 2.13-2.03 (m, 1H), 1.95-1.82 (m, 1H). $^{13}$C NMR (126 MHz, CDCl$_3$) δ 162.28, 147.11, 143.91, 140.60, 137.60, 135.05, 131.44, 128.71, 128.55, 127.20, 127.17, 126.96, 126.48, 126.27, 125.67, 125.29, 117.31, 115.65, 60.33, 58.58, 52.68, 50.03, 43.81, 35.27, 22.88. HRMS (ESI-TOF): m/z [M+H]+ calcd for C$_{26}$H$_{25}$N$_3$S: 412.1841, found: 412.1841.

Embodiment 15

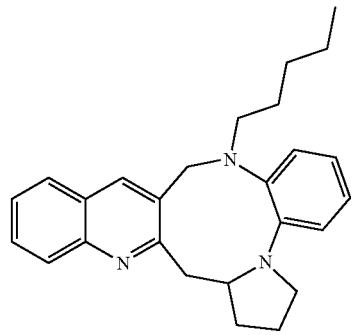

9-pentyl-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (51.7 mg, 0.6 mmol), PhCO$_2$H (24.4 mg, 0.2 mmol), afforded (12.4 mg, 16%) as a white oil after purification on silica gel (petroleum ether/EtOAc=100:1). $^1$H NMR (500 MHz, CDCl$_3$) δ 8.03 (dd, J=8.5, 1.0 Hz, 1H), 7.72 (s, 1H), 7.70 (dd, J=8.0, 1.5 Hz, 1H), 7.62 (ddd, J=8.5, 7.0, 1.5 Hz, 1H), 7.44 (ddd, J=8.0, 7.0, 1.5 Hz, 1H), 7.16 (dd, J=8.0, 1.5 Hz, 1H), 6.98 (ddd, J=8.5, 7.0, 1.5 Hz, 1H), 6.70 (td, J=7.5, 1.5 Hz, 1H), 6.55 (dd, J=8.5, 1.5 Hz, 1H), 4.83-4.69 (m, 1H), 4.35 (d, J=14.0 Hz, 1H), 4.27 (d, J=14.0 Hz, 1H), 3.33 (dd, J=13.0, 7.5 Hz, 1H), 3.26-3.16 (m, 2H), 3.14-3.05 (m, 1H), 3.02-2.91 (m, 1H), 2.90-2.80 (m, 1H), 2.21-2.05 (m, 3H), 1.95-1.83 (m, 1H), 1.52-1.39 (m, 2H), 1.25-1.19 (m, 2H), 1.19-1.11 (m, 2H), 0.81 (t, J=7.0 Hz, 3H). $^{13}$C NMR (126 MHz, CDCl$_3$) δ 162.57, 147.07, 144.34, 137.82, 134.56 (s, 2C), 132.24, 128.62 (s, 2C), 128.57 (s, 2C), 127.15 (s, 2C), 127.02, 126.44, 125.90 (s, 2C), 125.64 (s, 2C), 117.33, 115.53, 60.58, 60.45, 54.85, 49.89, 44.08, 34.95, 29.76, 26.54, 22.68, 22.55, 14.09. HRMS (ESI-TOF): m/z [M+H]+ calcd for C$_{26}$H$_{31}$N$_3$: 386.2590, found: 386.2590.

Embodiment 16

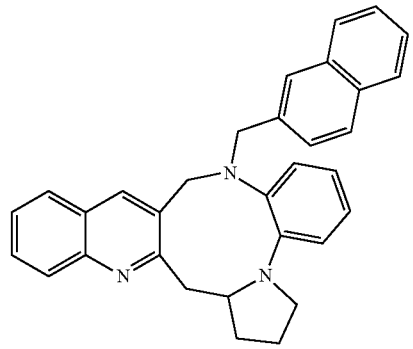

9-(naphthalen-2-ylmethyl)-2,3,9,10,17,17a-hexahydro-1H-benzo[2,3]pyrrolo[1',2':1,9][1,4]diazonino[7,6-b]quinoline: According to general procedure (for 48 h), quinolines (63.5 mg, 0.2 mmol), aldehydes (93.7 mg, 0.6 mmol), PhCO$_2$H (24.4 mg, 0.2 mmol), afforded (39.3 mg, 43%) as a white oil after purification on silica gel (petroleum ether/EtOAc=100:1). $^1$H NMR (500 MHz, CDCl$_3$) δ 7.18 (d, J=8.5 Hz, 1H), 6.96 (t, J=7.5 Hz, 2H), 6.93 (d, J=8.0 Hz, 1H), 6.83 (d, J=4.5 Hz, 2H), 6.79 (t, J=8.0 Hz, 2H), 6.66-6.55 (m, 3H), 6.49 (d, J=8.5 Hz, 1H), 6.26 (d, J=7.5 Hz, 1H), 6.12 (t, J=8.0 Hz, 1H), 5.90 (t, J=7.5 Hz, 1H), 5.83 (d, J=8.0 Hz, 1H), 3.80 (d, J=14.5 Hz, 1H), 3.74-3.65 (m, 1H), 3.56 (d, J=14.5 Hz, 1H), 3.43 (dd, J=25, 14.5 Hz, 2H), 2.51 (dd, J=13.0, 6.5 Hz, 1H), 2.39-2.25 (m, 1H), 2.21 (q, J=6.5 Hz, 1H), 1.38-1.28 (m, 1H), 1.23-1.13 (m, 2H), 1.01-0.93 (m, 1H). $^{13}$C NMR (126 MHz, CDCl$_3$) δ 162.05, 146.99, 143.16, 139.98, 135.38, 135.20, 133.29, 132.63, 131.74, 128.70, 128.53, 127.95, 127.88, 127.73, 127.64, 127.57, 127.09, 126.95, 126.01, 125.69, 125.56, 125.07, 118.83, 117.18, 61.56, 58.14 (d, J=3.8 Hz, 1C), 50.36, 43.12, 34.30, 26.91, 23.20. HRMS (ESI-TOF): m/z [M+H]+ calcd for C$_{32}$H$_{29}$N$_3$: 456.2434, found: 456.2435.

Embodiment 17

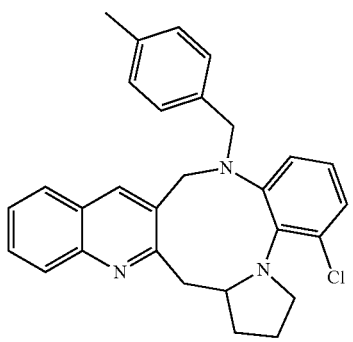

5-chloro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (70.4 mg, 0.2 mmol), aldehydes (72.1 mg, 0.6 mmol), PhCO$_2$H (24.4 mg, 0.2 mmol), afforded (44.1 mg, 61%) as a white oil after purification on silica gel (petroleum ether/EtOAc=75:1). $^1$H NMR (500 MHz, DMSO) δ 8.04 (s, 1H), 7.84 (d, J=8.5 Hz, 1H), 7.80 (dd, J=8.0, 1.0 Hz, 1H), 7.61 (ddd, J=8.5, 7.0, 1.5 Hz, 1H), 7.45 (ddd, J=8.0, 7.0, 1.0 Hz, 1H), 7.33 (d, J=7.5 Hz, 2H), 7.18 (d, J=7.5 Hz, 2H), 6.85-6.74 (m, 2H), 6.71-6.61 (m, 1H), 5.33 (s, 1H), 4.72 (d, J=15.0 Hz, 1H), 4.58 (d, J=15.0 Hz, 1H), 4.34 (d, J=14.0 Hz, 1H), 3.98 (t, J=8.0 Hz, 1H), 3.37 (s, 1H), 3.37-3.20 (m, 2H), 3.01 (s, 2H), 2.29 (s, 4H), 2.08-1.88 (m, 2H), 1.73 (s, 1H). $^{13}$C NMR (126 MHz, DMSO) δ 160.32, 151.76, 146.86, 136.80, 136.58, 136.28, 134.80, 132.16, 129.57 (s, 2C), 129.40, 128.59, 128.38, 127.82, 127.34, 126.81, 126.20, 121.96, 119.29, 63.22, 58.30, 53.68, 51.69, 43.56, 31.68, 25.31, 21.16. HRMS (ESI-TOF): m/z [M+H]+ calcd for C$_{29}$H$_{28}$ClN$_3$: 454.2044, found: 454.2043.

Embodiment 18

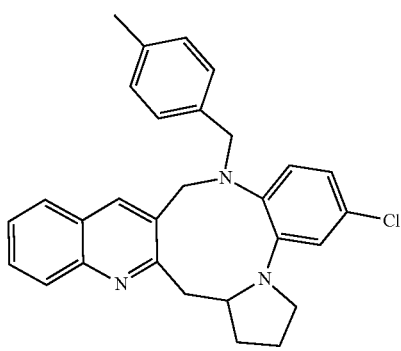

6-chloro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (70.4 mg, 0.2 mmol), aldehydes (72.1 mg, 0.6 mmol), PhCO$_2$H (24.4 mg, 0.2 mmol), afforded (45.2 mg, 50%) as a white oil after purification on silica gel (petroleum ether/EtOAc=50:1). $^1$H NMR (500 MHz, CDCl$_3$) δ 8.00 (d, J=8.0 Hz, 1H), 7.68 (dd, J=8.5, 1.5 Hz, 1H), 7.66 (s, 1H), 7.62 (ddd, J=8.5, 6.5, 1.5 Hz, 1H), 7.44 (ddd, J=8.0, 6.5, 1.0 Hz, 1H), 7.10 (q, J=8.0 Hz, 4H), 6.95 (d, J=8.0 Hz, 1H), 6.60 (dd, J=8.5, 2.5 Hz, 1H), 6.43 (d, J=2.5 Hz, 1H), 4.77-4.68 (m, 1H), 4.35 (d, J=14.0 Hz, 1H), 4.15 (d, J=14.0 Hz, 1H), 3.98 (q, J=13.5 Hz, 2H), 3.27 (dd, J=12.5, 7.5 Hz, 1H), 3.12-3.02 (m, 2H), 2.98-2.90 (m, 1H), 2.33 (s, 3H), 2.24-2.08 (m, 2H), 2.08-1.99 (m, 2H), 1.91-1.81 (m, 1H). $^{13}$C NMR (126 MHz, CDCl$_3$) δ 161.95, 147.12, 144.80, 136.93, 136.80, 135.06, 134.18, 131.24, 131.09, 129.72 (s, 2C), 128.96 (s, 2C), 128.77, 128.54, 127.79, 127.16, 126.90, 125.75, 116.86, 115.10, 60.10, 58.79, 58.36, 50.02, 43.80, 35.37, 22.76, 21.12. HRMS (ESI-TOF): m/z [M+H]+ calcd for C$_{29}$H$_{28}$ClN$_3$: 454.2044, found: 454.2043.

Embodiment 19

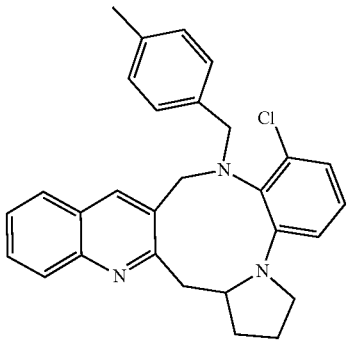

8-chloro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (70.4 mg, 0.2 mmol), aldehydes (72.1 mg, 0.6 mmol), PhCO$_2$H (24.4 mg, 0.2 mmol), afforded (46.7 mg, 52%) as a white oil after purification on silica gel (petroleum ether/EtOAc=100:1). $^1$H NMR (500 MHz, CDCl$_3$) δ 8.07 (d, J=8.5 Hz, 1H), 7.90 (s, 1H), 7.79 (d, J=8.0 Hz, 1H), 7.67 (t, J=7.5 Hz, 1H), 7.50 (t, J=7.5 Hz, 1H), 6.95 (t, J=8.0 Hz, 2H), 6.87 (d, J=8.0 Hz, 2H), 6.73 (dd, J=8.1, 3.3 Hz, 3H), 6.44 (d, J=8.5 Hz, 1H), 4.59 (d, J=15.5 Hz, 1H), 4.48 (d, J=15.5 Hz, 1H), 4.30 (q, J=7.0, 6.5 Hz, 1H), 4.10 (d, J=12.5 Hz, 1H), 3.78 (d, J=12.5 Hz, 1H), 3.36 (dd, J=16.0, 8.0 Hz, 1H), 3.31 (d, J=13.0 Hz, 1H), 2.93-2.84 (m, 1H), 2.76 (dd, J=13.0, 7.0 Hz, 1H), 2.31-2.16 (m, 5H), 2.01-1.87 (m, 3H). $^{13}$C NMR (126 MHz, CDCl$_3$) δ 162.44, 147.15, 147.11, 138.17, 136.50, 135.01, 134.01, 132.47, 132.23, 130.04 (s, 2C), 128.80, 128.72, 128.69, 128.18 (s, 2C), 127.35, 127.30, 125.81, 118.15, 114.66, 59.69, 59.24, 56.24, 50.55, 42.21, 35.28, 23.26, 21.01. HRMS (ESI-TOF): m/z [M+H]+ calcd for C$_{29}$H$_{28}$ClN$_3$: 454.2044, found: 454.2044.

Embodiment 20

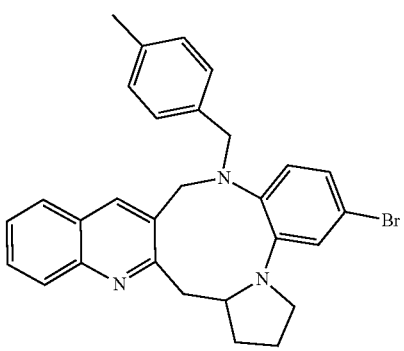

6-bromo-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (79.3 mg, 0.2 mmol), aldehydes (72.1 mg, 0.6 mmol), PhCO$_2$H (24.4 mg, 0.2 mmol), afforded (39.8 mg, 40%) as a white oil after purification on silica gel (petroleum ether/EtOAc=100:1). $^1$H NMR (500 MHz, CDCl$_3$) δ 8.00 (d, J=8.5 Hz, 1H), 7.71-7.65 (m, 2H), 7.62 (ddd, J=8.5, 7.0, 1.5 Hz, 1H), 7.44 (ddd, J=8.0, 6.5, 1.0 Hz, 1H), 7.12 (d, J=8.0 Hz, 2H), 7.08 (d, J=8.0 Hz, 2H), 6.89 (d, J=8.5 Hz, 1H), 6.75 (dd, J=8.0, 2.0 Hz, 1H), 6.60 (d, J=2.5 Hz, 1H), 4.74-4.62 (m, 1H), 4.35 (d, J=13.5 Hz, 1H), 4.20 (d, J=13.5 Hz, 1H), 3.98 (dd, J=13.0 Hz, 2H), 3.28 (dd, J=12.5, 7.5 Hz, 1H), 3.14-3.02 (m, 2H), 2.98-2.88 (m, 1H), 2.33 (s, 3H), 2.20-2.08 (m, 2H), 2.07-1.98 (m, 1H), 1.89-1.79 (m, 1H). $^{13}$C NMR (126 MHz, CDCl$_3$) δ 161.89, 147.10, 144.97, 137.51, 136.93, 135.09, 134.14, 131.22, 129.65 (s, 2C), 128.98 (s, 2C), 128.78, 128.55, 128.00, 127.16, 126.90, 125.77, 120.04, 119.09, 118.24, 60.31, 58.60, 58.15, 50.08, 43.70, 35.24, 22.82, 21.12. HRMS (ESI-TOF): m/z [M+H]$^+$ calcd for C$_{29}$H$_{28}$BrN$_3$: 498.1539, found: 498.1539.

Embodiment 21

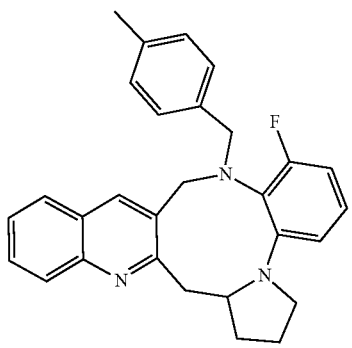

8-fluoro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (67.1 mg, 0.2 mmol), aldehydes (72.1 mg, 0.6 mmol), PhCO$_2$H (24.4 mg, 0.2 mmol), afforded (42.9 mg, 50%) as a white oil after purification on silica gel (petroleum ether/EtOAc=100:1). $^1$H NMR (500 MHz, CDCl$_3$) δ 8.04 (d, J=8.0 Hz, 1H), 7.79 (s, 1H), 7.75 (d, J=8.0 Hz, 1H), 7.65 (t, J=7.5 Hz, 1H), 7.48 (t, J=7.5 Hz, 1H), 7.01-6.92 (m, 3H), 6.85 (d, J=7.5 Hz, 2H), 6.41 (dd, J=11.0, 8.5 Hz, 1H), 6.27 (d, J=8.5 Hz, 1H), 4.68-4.50 (m, 1H), 4.45 (d, J=14.5 Hz, 1H), 4.36 (d, J=14.5 Hz, 1H), 3.97 (d, J=12.5 Hz, 1H), 3.87 (d, J=12.5 Hz, 1H), 3.26 (d, J=12.5 Hz, 2H), 3.02 (td, J=8.0, 4.5 Hz, 1H), 2.86 (dd, J=12.5, 7.0 Hz, 1H), 2.34-2.13 (m, 4H), 2.10-2.00 (m, 2H), 1.77-1.63 (m, 1H). $^{13}$C NMR (126 MHz, CDCl$_3$) δ 162.36, 147.06, 146.28, 136.58, 134.60, 134.36, 132.40, 129.83, 128.75 (d, J=6.9), 128.63, 128.45 (s, 2C), 127.25 (s, 2C), 127.14 (d, J=3.3 Hz), 127.04, 125.75, 123.58 (d, J=16.5 Hz, 1C), 110.85, 103.43, 103.26, 59.46, 58.46, 57.40, 50.17, 42.74, 35.27, 22.95, 21.06. $^{19}$F NMR (470 MHz, CDCl$_3$) δ −119.95. HRMS (ESI-TOF): m/z [M+H]$^+$ calcd for C$_{29}$H$_{28}$FN$_3$: 438.2340, found: 438.2341.

Embodiment 22

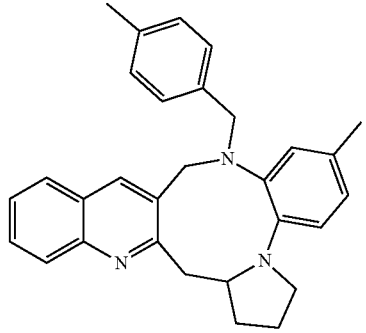

7-methyl-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (66.3 mg, 0.2 mmol), aldehydes (72.1 mg, 0.6 mmol), PhCO$_2$H (24.4 mg, 0.2 mmol), afforded (55 mg, 63%) as a white oil after purification on silica gel (petroleum ether/EtOAc=100:1). $^1$H NMR (500 MHz, CDCl$_3$) δ 8.01 (d, J=8.5 Hz, 1H), 7.68-7.62 (m, 2H), 7.61 (td, J=8.5, 7.0, 1.5 Hz, 2H), 7.42 (td, J=8.0, 7.0, 1.5 Hz, 1H), 7.11 (s, 4H), 6.83 (d, J=2.0 Hz, 1H), 6.77-6.68 (m, 2H), 4.88 (d, J=14.5 Hz, 1H), 4.28 (d, J=14.5 Hz, 1H), 4.25-4.19 (m, 1H), 4.18 (d, J=14.5 Hz, 1H), 4.07 (d, J=14.5 Hz, 1H), 3.46 (dd, J=13.0, 6.0 Hz, 1H), 3.23-3.12 (m, 1H), 3.10 (dd, J=13.0, 3.0 Hz, 1H), 3.07-2.97 (m, 1H), 2.32 (s, 3H), 2.22 (s, 3H), 2.17-2.05 (m, 1H), 1.98-1.73 (m, 3H). $^{13}$C NMR (126 MHz, CDCl$_3$) δ 161.94, 146.98, 141.82, 140.18, 136.59, 135.27, 135.00, 132.17, 129.62, 129.01 (s, 2C), 128.95 (s, 2C), 128.65, 128.58, 127.04, 127.02, 125.63, 124.64, 124.56, 118.75, 62.89, 57.33, 57.13, 51.00, 42.73, 33.23, 23.54, 21.07, 20.62. HRMS (ESI-TOF): m/z [M+H]$^+$ calcd for C$_{30}$H$_{31}$N$_3$: 434.2590, found: 434.2590.

Embodiment 23

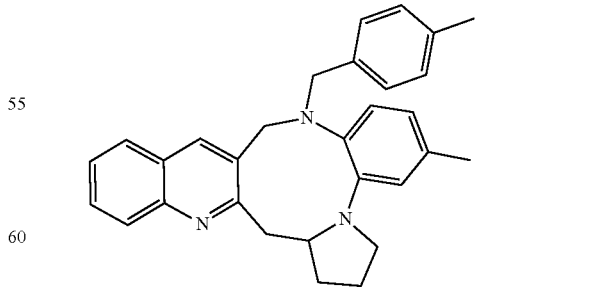

6-methyl-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (66.3 mg, 0.2 mmol), aldehydes (72.1 mg, 0.6 mmol), PhCO₂H (24.4 mg, 0.2 mmol), afforded (41.1 mg, 48%) as a white oil after purification on silica gel (petroleum ether/EtOAc=100:1). ¹H NMR (500 MHz, CDCl₃) δ 8.00 (d, J=8.5 Hz, 1H), 7.68-7.62 (m, 2H), 7.61 (ddd, J=8.5, 6.5, 1.5 Hz, 2H), 7.42 (td, J=8.0, 7.0, 1.5 Hz, 1H), 7.11 (s, 4H), 6.95 (d, J=8.0 Hz, 1H), 6.51 (dd, J=8.0, 2.0 Hz, 1H), 6.38 (d, J=2.0 Hz, 1H), 4.74-4.49 (m, 1H), 4.37-4.27 (m, 2H), 4.10-3.95 (m, 2H), 3.28 (dd, J=13.0, 7.5 Hz, 1H), 3.20-3.08 (m, 2H), 3.08-2.97 (m, 1H), 2.32 (s, 3H), 2.21 (s, 3H), 2.18-2.08 (m, 2H), 2.08-1.97 (m, 1H), 1.89-1.78 (m, 2H). ¹³C NMR (126 MHz, CDCl₃) δ 162.35, 147.01, 143.27, 136.70, 136.66, 135.00, 134.90, 134.80, 131.88, 129.62 (s, 2C), 128.87 (s, 2C), 128.55 (s, 2C), 127.12, 126.95, 126.20, 125.55, 118.62, 116.71, 60.62, 58.47, 58.26, 50.11, 43.67, 34.95, 23.00, 21.34, 21.11. HRMS (ESI-TOF): m/z [M+H]⁺ calcd for $C_{30}H_{31}N_3$: 434.2590, found: 434.2591.

Embodiment 25

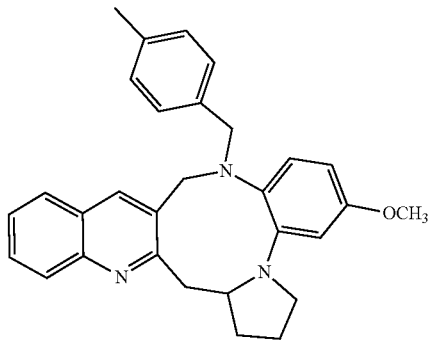

6-methoxy-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (69.5 mg, 0.2 mmol), aldehydes (72.1 mg, 0.6 mmol), PhCO₂H (24.4 mg, 0.2 mmol), afforded (43.1 mg, 46%) as a white oil after purification on silica gel (petroleum ether/EtOAc=50:1). ¹H NMR (500 MHz, CDCl₃) δ 7.99 (d, J=8.5 Hz, 1H), 7.66 (dd, J=8.5, 1.5 Hz, 1H), 7.63 (s, 1H), 7.61 (ddd, J=8.5, 7.0, 1.5 Hz, 1H), 7.43 (ddd, J=8.0, 7.0, 1.5 Hz, 1H), 7.11 (s, 4H), 6.99 (d, J=8.5 Hz, 1H), 6.21 (dd, J=8.5, 3.0 Hz, 1H), 5.98 (d, J=3.0 Hz, 1H), 4.85 (s, 1H), 4.35 (d, J=14.0 Hz, 1H), 4.04 (d, J=14.0 Hz, 1H), 4.00 (d, J=13.0 Hz, 1H), 3.92 (d, J=13.0 Hz, 1H), 3.72 (s, 3H), 3.26-3.16 (m, 1H), 3.15-3.05 (m, 2H), 3.02-2.93 (m, 1H), 2.33 (s, 3H), 2.29-2.18 (m, 1H), 2.17-2.03 (m, 3H), 1.90-1.80 (m, 1H). ¹³C NMR (126 MHz, CDCl₃) δ 162.40, 157.95, 147.11, 145.13, 136.74, 134.79, 134.69, 131.72, 131.62, 129.97 (s, 2C), 128.84 (s, 2C), 128.57, 128.53, 128.04, 127.17, 126.95, 125.56, 101.12, 100.71, 59.59, 59.32, 59.12, 55.10, 49.84, 44.18, 35.71, 22.61, 21.13. HRMS (ESI-TOF): m/z [M+H]⁺ calcd for $C_{30}H_{31}N_3O$: 450.2539, found: 450.2540.

Embodiment 24

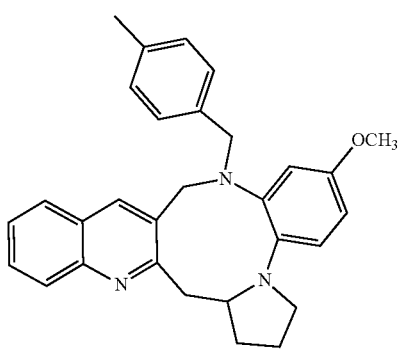

7-methoxy-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (69.5 mg, 0.2 mmol), aldehydes (72.1 mg, 0.6 mmol), PhCO₂H (24.4 mg, 0.2 mmol), afforded (48.5 mg, 54%) as a white oil after purification on silica gel (petroleum ether/EtOAc=20:1). ¹H NMR (500 MHz, CDCl₃) δ 8.02 (d, J=8.5 Hz, 1H), 7.68 (s, 1H), 7.67-7.59 (m, 2H), 7.43 (t, J=7.5 Hz, 1H), 7.13 (q, J=8.0 Hz, 4H), 7.00 (d, J=9.0 Hz, 1H), 6.52 (d, J=2.5 Hz, 1H), 6.44 (dd, J=8.5, 2.5 Hz, 1H), 5.63 (d, J=15.0 Hz, 1H), 4.36 (d, J=15.5 Hz, 1H), 4.23 (d, J=15.0 Hz, 1H), 4.18 (d, J=16.0 Hz, 1H), 3.76-3.62 (m, 5H), 3.26-3.13 (m, 1H), 3.11-2.96 (m, 2H), 2.32 (s, 3H), 2.13-2.03 (m, 1H), 1.82-1.72 (m, 2H), 1.63-1.51 (m, 1H). ¹³C NMR (126 MHz, CDCl₃) δ 161.23, 155.90, 146.71, 146.34, 136.51, 135.91, 134.80, 134.53, 132.32, 129.14 (s, 2C), 128.72, 128.54, 127.98 (s, 2C), 126.95 (s, 2C), 125.79, 122.81, 106.65, 106.21, 65.75, 55.87, 55.49, 55.37, 52.13, 41.66, 30.85, 24.14, 21.06. HRMS (ESI-TOF): m/z [M+H]⁺ calcd for $C_{30}H_{31}N_3O$: 450.2539, found: 450.2539.

Embodiment 26

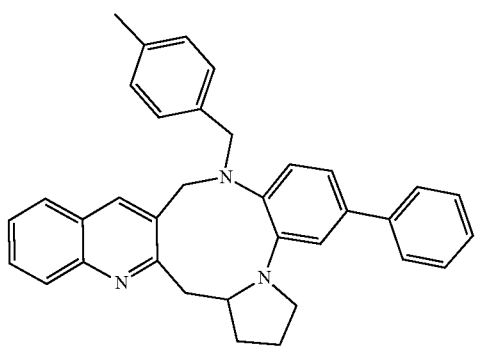

9-(4-methylbenzyl)-6-phenyl-2,3,9,10,17,17a-hexahydro-1H-benzo[2,3]pyrrolo[1',2':1,9][1,4]diazonino[7,6-b]quinoline: According to general procedure (for 48 h), quinolines (78.7 mg, 0.2 mmol), aldehydes (72.1 mg, 0.6 mmol), PhCO₂H (24.4 mg, 0.2 mmol), afforded (48.9 mg, 50%) as a white oil after purification on silica gel (petroleum ether/EtOAc=100:1). ¹H NMR (500 MHz, CDCl₃) δ 8.01 (d, J=8.0 Hz, 1H), 7.67-7.63 (m, 2H), 7.61 (ddd, J=8.5, 7.0, 1.5 Hz, 1H), 7.51-7.47 (m, 2H), 7.42 (ddd, J=8.0, 6.5, 1.0 Hz, 1H), 7.38 (t, J=7.5 Hz, 2H), 7.30 (d, J=2.0 Hz, 1H), 7.26-7.23 (m, 1H), 7.21 (dd, J=8.0, 2.0 Hz, 1H), 7.16-7.09

(m, 4H), 6.60 (d, J=8.5 Hz, 1H), 4.77-4.66 (m, 1H), 4.43-4.33 (m, 2H), 4.15-4.01 (m, 2H), 3.32 (dd, J=12.5, 7.0 Hz, 1H), 3.22-3.13 (m, 2H), 3.08-3.02 (m, 1H), 2.33 (s, 3H), 2.21-2.10 (m, 2H), 2.10-2.03 (m, 1H), 1.91-1.82 (m, 1H). $^{13}$C NMR (126 MHz, CDCl$_3$) δ 162.19, 147.14, 143.01, 141.13, 138.95, 136.83, 135.02, 134.61, 131.68, 130.39, 129.72 (s, 2C), 128.95 (s, 2C), 128.63 (s, 2C), 128.61, 127.15, 126.99, 126.30, 126.14 (s, 2C), 125.99, 125.65, 125.18, 124.21, 116.32, 60.64, 58.62, 58.26, 50.17, 43.72, 34.98, 22.95, 21.10. HRMS (ESI-TOF): m/z [M+H]$^+$ calcd for C$_{35}$H$_{33}$N$_3$: 496.2747, found: 496.2746.

Embodiment 27

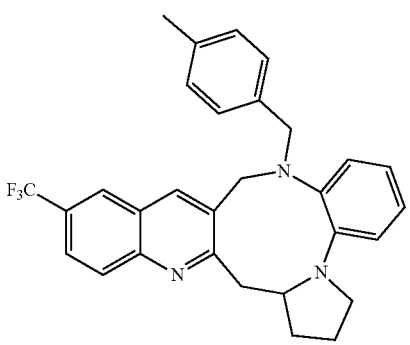

9-(4-methylbenzyl)-13-(trifluoromethyl)-2,3,9,10,17,17a-hexahydro-1H-benzo[2,3]pyrrolo[1',2':1,9][1,4]diazonino[7,6-b]quinoline: According to general procedure (for 48 h), quinolines (77.1 mg, 0.2 mmol), aldehydes (72.1 mg, 0.6 mmol), PhCO$_2$H (24.4 mg, 0.2 mmol), afforded (62.6 mg, 64%) as a yellow oil after purification on silica gel (petroleum ether/EtOAc=200:1). $^1$H NMR (500 MHz, CDCl$_3$) δ 8.08 (d, J=9.0 Hz, 1H), 7.93 (d, J=2.0 Hz, 1H), 7.76 (dd, J=9.0, 2.5 Hz, 1H), 7.65 (s, 1H), 7.15-7.07 (m, 5H), 6.94 (ddd, J=8.5, 7.0, 1.5 Hz, 1H), 6.71 (td, J=7.0, 1.0 Hz, 1H), 6.57 (dd, J=8.5, 1.5 Hz, 1H), 4.74-4.61 (m, 1H), 4.42-4.32 (m, 2H), 4.12-4.04 (m, 2H), 3.38 (dd, J=12.5, 7.0 Hz, 1H), 3.19-3.08 (m, 2H), 2.99-2.91 (m, 1H), 2.31 (s, 3H), 2.17-2.05 (m, 2H), 2.04-1.97 (m, 1H), 1.90-1.82 (m, 1H). $^{13}$C NMR (126 MHz, CDCl$_3$) δ 164.76, 147.97, 143.46, 139.51, 136.93, 135.41, 134.56, 133.34, 129.67, 129.60 (s, 2C), 129.00 (s, 2C), 125.89, 125.77, 125.55, 125.11 (q, 4.2 Hz, 2C), 124.31 (q, 3.4 Hz, 1C), 118.45, 116.54, 61.02, 58.60, 58.42, 50.30, 43.71, 34.82, 23.05, 21.06. $^{19}$F NMR (470 MHz, CDCl$_3$) δ −62.11. HRMS (ESI-TOF): m/z [M+H]$^+$ calcd for C$_{30}$H$_{28}$F$_3$N$_3$: 488.2308, found: 488.2307.

Embodiment 28

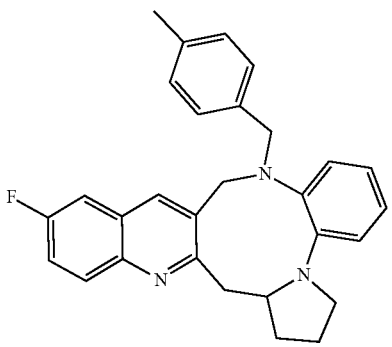

13-fluoro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (67.1 mg, 0.2 mmol), aldehydes (72.1 mg, 0.6 mmol), PhCO$_2$H (24.4 mg, 0.2 mmol), afforded (46.3 mg, 53%) as a white oil after purification on silica gel (petroleum ether/EtOAc=100:1). $^1$H NMR (500 MHz, CDCl$_3$) δ 7.98 (dd, J=9.5, 5.5 Hz, 1H), 7.57 (s, 1H), 7.36 (td, J=8.5, 3.0 Hz, 1H), 7.27-7.23 (m, 1H), 7.10 (s, 4H), 7.05 (dd, J=8.0, 2.0 Hz, 1H), 6.94 (ddd, J=9.0, 7.5, 2.0 Hz, 1H), 6.71 (td, J=7.5, 1.5 Hz, 1H), 6.61 (dd, J=8.0, 1.5 Hz, 1H), 4.58-4.52 (m, 1H), 4.46 (d, J=14.0 Hz, 1H), 4.33 (d, J=14.0 Hz, 1H), 4.11-4.01 (m, 2H), 3.32 (dd, J=12.5, 6.5 Hz, 1H), 3.18-3.12 (m, 1H), 3.09 (dd, J=12.5, 2.5 Hz, 1H), 3.03-2.96 (m, 1H), 2.32 (s, 3H), 2.17-2.09 (m, 1H), 2.07-1.93 (m, 2H), 1.89-1.80 (m, 1H). $^{13}$C NMR (126 MHz, CDCl$_3$) δ 161.46 (d, J=2.6 Hz, 1C), 161.03, 159.07, 144.09, 143.32, 139.77, 136.78, 134.65, 134.35 (d, J=5.2 Hz, 1C), 132.79, 130.93 (d, J=9.1 Hz, 1C), 129.46, 128.94, 127.50 (d, J=10.0 Hz, 1C), 125.68, 125.23, 118.57 (t, J=12.8 Hz, 1C), 116.83, 110.08 (d, J=21.5 Hz, 1C), 61.23, 58.18, 58.06, 50.34, 43.26, 34.56, 23.14, 21.08. $^{19}$F NMR (470 MHz, CDCl$_3$) δ −115.03. HRMS (ESI-TOF): m/z [M+H]$^+$ calcd for C$_{29}$H$_{28}$FN$_3$: 438.2340, found: 438.2399.

Embodiment 29

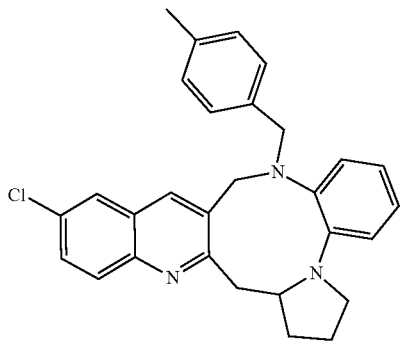

13-chloro-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (70.4 mg, 0.2 mmol), aldehydes (72.1 mg, 0.6 mmol), PhCO$_2$H (24.4 mg, 0.2 mmol), afforded (50.2 mg, 55%) as a white oil after purification on silica gel (petroleum ether/EtOAc=100:1). $^1$H NMR (500 MHz, Chloroform-d) δ 7.91 (d, J=8.5 Hz, 1H), 7.59 (d, J=2.5 Hz, 1H), 7.54-7.48 (m, 2H), 7.10 (s, 4H), 7.06 (dd, J=8.0, 1.5 Hz, 1H), 6.93 (ddd, J=8.5, 7.5, 2.0 Hz, 1H), 6.70 (td, J=7.5, 1.5 Hz, 1H), 6.58 (dd, J=8.0, 1.5 Hz, 1H), 4.64-4.53 (m, 1H), 4.41 (d, J=14.0 Hz, 1H), 4.32 (d, J=14.0 Hz, 1H), 4.06 (s, 2H), 3.33 (dd, J=13.0, 7.0 Hz, 1H), 3.17-3.11 (m, 1H), 3.08 (dd, J=13.0, 3.0 Hz, 1H), 3.00-2.93 (m, 1H), 2.32 (s, 3H), 2.16-2.04 (m, 3H), 2.01-1.93 (m, 1H), 1.88-1.80 (m, 1H). $^{13}$C NMR (126 MHz, Chloroform-d) δ 162.55, 145.39, 143.38, 139.62, 136.82, 134.63, 133.96, 132.90, 131.19, 130.21, 129.50 (s, 2C), 129.42, 128.96 (s, 2C), 127.56, 125.76, 125.71, 125.36, 118.47, 116.67, 61.10, 58.28, 50.30, 43.46, 34.68, 23.09, 21.08. HRMS (ESI-TOF): m/z [M+H]$^+$ calcd for C$_{29}$H$_{28}$ClN$_3$: 454.2044, found: 454.2045.

Embodiment 30

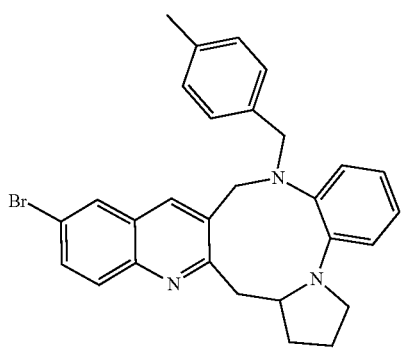

13-bromo-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (79.3 mg, 0.2 mmol), aldehydes (72.1 mg, 0.6 mmol), PhCO$_2$H (24.4 mg, 0.2 mmol), afforded (38.4 mg, 39%) as a white oil after purification on silica gel (petroleum ether/EtOAc=100:1). $^1$H NMR (500 MHz, CDCl$_3$) δ 7.85 (d, J=9.0 Hz, 1H), 7.77 (d, J=2.5 Hz, 1H), 7.65 (dd, J=9.0, 2.0 Hz, 1H), 7.50 (s, 1H), 7.11 (s, 4H), 7.07 (dd, J=8.0, 2.0 Hz, 1H), 6.93 (ddd, J=9.0, 7.5, 2.0 Hz, 1H), 6.70 (td, J=7.5, 1.5 Hz, 1H), 6.58 (dd, J=8.5, 1.5 Hz, 1H), 4.67-4.54 (m, 1H), 4.40 (d, J=14.0 Hz, 1H), 4.33 (d, J=14.0 Hz, 1H), 4.06 (s, 2H), 3.32 (dd, J=12.5, 7.0 Hz, 1H), 3.17-3.11 (m, 1H), 3.08 (dd, J=12.5, 3.0 Hz, 1H), 3.00-2.93 (m, 1H), 2.32 (s, 3H), 2.15-2.06 (m, 2H), 2.02-1.94 (m, 1H), 1.89-1.80 (m, 1H). $^{13}$C NMR (126 MHz, CDCl$_3$) δ 161.66, 144.44, 142.24, 138.39, 135.78, 133.48, 132.83, 131.77, 130.93, 129.21, 128.45 (s, 2C), 128.05, 127.91 (s, 2C), 127.01, 124.64, 124.32, 118.22, 117.27, 115.41, 59.89, 57.18 (s, 2C), 49.17, 42.38, 33.66, 21.99, 20.05. HRMS (ESI-TOF): m/z [M+H]+ calcd for C$_{29}$H$_{28}$BrN$_3$: 498.1539, found: 498.1538.

Embodiment 31

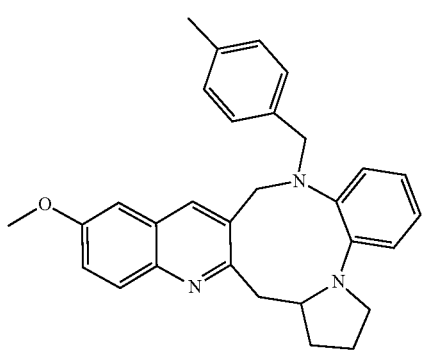

13-methoxy-9-(4-methylbenzyl)-2,3,9,10,17,17a-hexahydro-1H-benzo[2,3]pyrrolo[1',2':1,9][1,4]diazonino[7,6-b]quinoline: According to general procedure (for 48 h), quinolines (69.5 mg, 0.2 mmol), aldehydes (72.1 mg, 0.6 mmol), PhCO$_2$H (24.4 mg, 0.2 mmol), afforded (38.2 mg, 43%) as a white oil after purification on silica gel (petroleum ether/EtOAc=100:1). $^1$H NMR (500 MHz, CDCl$_3$) δ 7.90 (d, J=9.0 Hz, 1H), 7.57 (s, 1H), 7.27 (dd, J=9.0, 2.5 Hz, 1H), 7.11 (s, 4H), 7.03 (dd, J=8.0, 1.5 Hz, 1H), 6.97-6.92 (m, 2H), 6.71 (td, J=7.5, 1.5 Hz, 1H), 6.64 (dd, J=8.0, 1.5 Hz, 1H), 4.51 (d, J=14.0 Hz, 1H), 4.49-4.44 (m, 1H), 4.32 (d, J=14.0 Hz, 1H), 4.09-4.01 (m, 2H), 3.90-3.87 (m, 3H), 3.30 (dd, J=13.0, 7.0 Hz, 1H), 3.21-3.12 (m, 1H), 3.11-3.05 (m, 1H), 3.05-2.98 (m, 1H), 2.33 (s, 3H), 2.18-2.09 (m, 1H), 2.05-1.93 (m, 2H), 1.88-1.79 (m, 1H). $^{13}$C NMR (126 MHz, CDCl$_3$) δ 159.52, 157.25, 143.29, 143.08, 139.99, 136.65, 134.81, 134.14, 132.12, 130.04, 129.40 (s, 2C), 128.91 (s, 2C), 127.84, 125.62, 124.98, 120.99, 118.57, 117.01, 105.01, 61.45, 58.10, 57.70, 55.48, 50.38, 43.06, 34, 41, $^{13}$C NMR (126 MHz, Chloroform-d) δ 159.52, 157.25, 143.29, 143.08, 139.99, 136.65, 134.81, 134.14, 132.12, 130.04, 129.40, 128.91, 127.84, 125.62, 124.98, 120.99, 118.57, 117.01, 105.01, 61.45, 58.10, 57.70, 55.48, 50.38, 43.06, 34.41, 23.21, 21.10. HRMS (ESI-TOF): m/z [M+H]+ calcd for C$_{30}$H$_{31}$N$_3$O: 450.2539, found: 450.2538.

The above descriptions are merely the preferred embodiments of the present disclosure, which are not intended to limit the present disclosure in other forms. Any person skilled in the art may change or modify the disclosed technical contents as equivalent embodiments of equivalent changes. However, any simple amendment, equivalent change, and variation made to the embodiments according to the technical substance of the present disclosure, without deviating from the technical solution of the present disclosure, still fall within the protection scope of the technical solution of the present disclosure.

The invention claimed is:

1. A quinoline-2,3-fused nine-membered ring compound, structurally shown as follows:

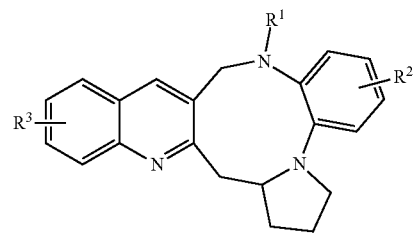

where:

R$^1$ is selected from benzyl, p-cyanobenzyl, p-trifluoromethylbenzyl, o-aldehydebenzyl, p-chlorobenzyl, m-methylbenzyl, 2-fluoro-4-chlorobenzyl, p-methoxybenzyl, furylmethyl, thenyl or menaphthyl;

R$^2$ is located at any feasible position of this benzene ring, and selected from halogen, phenyl, methyl or methoxy; and R$^3$ is located at any feasible position of this benzene ring, and selected from halogen, trifluoromethyl or methoxy.

2. A preparation method of the quinoline-2,3-fused nine-membered ring compound according to claim 1, comprising the following steps:

mixing a quinoline-derived aniline compound and a formaldehyde compound, adding a solvent and a catalyst, controlling a system temperature, and reacting with stirring to obtain the quinoline-2,3-fused nine-membered ring compound.

3. The preparation method according to claim 2, wherein the quinoline-derived aniline compound is selected from the following structure:

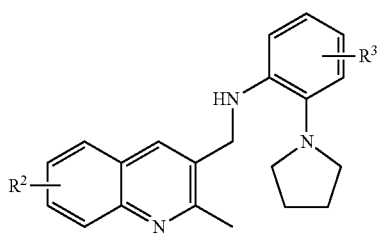

where:
R² is located at any feasible position of this benzene ring, and selected from halogen, trichloromethylor, methoxy; and R³ is located at any feasible position of this benzene ring, and =selected from halogen, phenyl, methyl or methoxy.

4. The preparation method according to claim 2, wherein the formaldehyde compound is selected from the following structure:

R¹—CHO where:
R¹ is selected from phenyl, p-cyanophenyl, p-trifluoromethylphenyl, o-aldehydephenyl, p-chlorophenyl, m-methylphenyl, 2-fluoro-4-chlorophenyl, p-methoxyphenyl, furan, thiophene or naphthalene.

5. The preparation method according to claim 2, wherein a molar ratio of the quinoline-derived aniline compound to the formaldehyde compound ranges from 1:1 to 1:4.

6. The preparation method according to claim 2, wherein the solvent is selected from any one of 1,2-dichloroethane, ethyl alcohol, 1,4-dioxane, ethyl acetate, hexafluoroisopropanol, acetonitrile and N,N-dimethylformamide.

7. The preparation method according to claim 2, wherein the catalyst is selected from any one of an acetic acid, a benzoic acid, a p-toluenesulfonic acid, a methanesulfonic acid, a trifluoromethanesulfonic acid, a camphorsulfonic acid, a trifluoroacetic acid, scandium trifluoromethanesulfonate and boron trifluoride diethyl etherate.

8. The preparation method according to claim 2, wherein the solvent is added in an amount of 10 L to 30 L per mole of quinoline-derived o-phenylenediamine compound.

9. The preparation method according to claim 2, wherein a reaction temperature ranges from 50° C. to 70° C.

10. A method of inhibiting fungal activity in plants comprising applying to plants a plant fungicide comprising an effective component of a compound of claim 1.

11. The method according to claim 10, wherein the plant fungicide is used for *C. gloeosporioides, V. mali, F. oxysporum, B. cinerea* and/or *G. graminis*.

12. A compound selected from compounds structurally shown as follows.

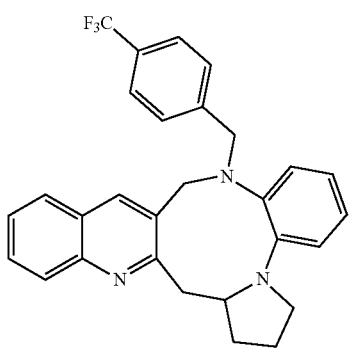

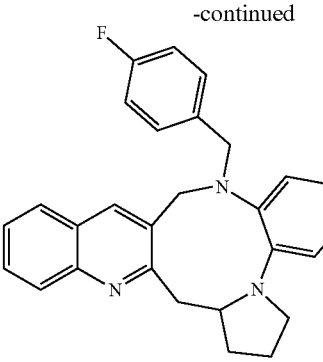

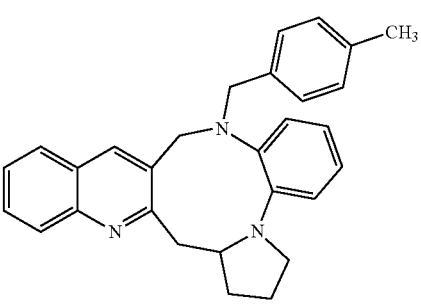

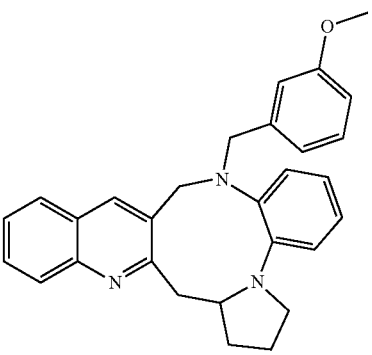

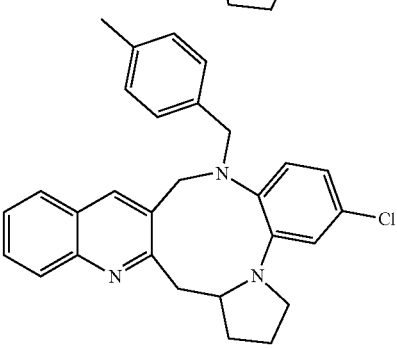

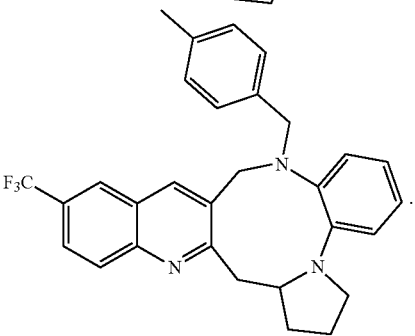

13. The method according to claim 10, wherein the plant fungicide further comprises pesticidally acceptable auxiliaries, additives, stabilizers, flavoring agents, emulsifiers or synergists.

14. The method according to claim 10, wherein an effective concentration of the plant fungicide ranges from 25 mg/L to 100 mg/L.

15. The method according to claim 10, wherein the plant fungicide is powder, a suspension agent, wettable powder, an emulsion, an emulsifiable solution, cream, paste, a colloid, a fumigant, a smoke generator, an aerosol, granules, fine granules or oil agents.

* * * * *